United States Patent
Lu et al.

(10) Patent No.: US 10,954,188 B2
(45) Date of Patent: *Mar. 23, 2021

(54) ISOTOPE-ENRICHED 3-AMINO-1-PROPANESULFONIC ACID DERIVATIVES AND USES THEREOF

(71) Applicant: RISEN (SUZHOU) PHARMA TECH CO., LTD., Suzhou (CN)

(72) Inventors: Jiasheng Lu, Shanghai (CN); Jiamin Gu, Suzhou (CN); Xinyong Lv, Suzhou (CN); Guowei Song, Suzhou (CN); Dongdong Wu, Suzhou (CN); Daiqiang Hu, Suzhou (CN); Jun Gu, Suzhou (CN); Gang Chen, Suzhou (CN); Xiang Ji, Suzhou (CN); Xiuchun Zhang, Suzhou (CN); Jinchao Ai, Suzhou (CN); Xianqi Kong, Dollard-des-Ormeaux (CA)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/655,311

(22) Filed: Oct. 17, 2019

(65) Prior Publication Data

US 2020/0223793 A1 Jul. 16, 2020

Related U.S. Application Data

(63) Continuation of application No. 15/476,255, filed on Mar. 31, 2017, now Pat. No. 10,472,323.

(30) Foreign Application Priority Data

Mar. 21, 2017 (CN) .......................... 201710168819.2

(51) Int. Cl.

| C07C 309/14 | (2006.01) |
|---|---|
| C07C 309/15 | (2006.01) |
| C07C 309/59 | (2006.01) |
| C07C 233/61 | (2006.01) |
| C07B 59/00 | (2006.01) |
| C07D 233/61 | (2006.01) |

(52) U.S. Cl.
CPC .......... *C07C 309/14* (2013.01); *C07B 59/001* (2013.01); *C07B 59/002* (2013.01); *C07C 309/15* (2013.01); *C07C 309/59* (2013.01); *C07D 233/61* (2013.01); *C07B 2200/05* (2013.01)

(58) Field of Classification Search
CPC ... C07C 309/14; C07C 309/54; C07C 309/15; C07C 233/61

See application file for complete search history.

(56) References Cited

U.S. PATENT DOCUMENTS

| 5,840,294 | A | 11/1998 | Kisilevsky et al. |
|---|---|---|---|
| 5,972,328 | A | 10/1999 | Kisilevsky et al. |
| 6,310,073 | B1 | 10/2001 | Kisilevsky et al. |
| 6,603,008 | B1 | 8/2003 | Ando et al. |
| 6,670,399 | B2 | 12/2003 | Green et al. |
| 7,253,306 | B2 | 8/2007 | Kong et al. |
| 7,414,076 | B2 | 8/2008 | Kong et al. |
| 7,517,990 | B2 | 4/2009 | Ito et al. |
| 7,851,641 | B2 | 12/2010 | Findeis |
| 8,044,100 | B2 | 10/2011 | Kong et al. |
| 8,642,801 | B2 | 2/2014 | Kong et al. |
| 8,748,656 | B2 | 6/2014 | Kong et al. |
| 8,835,500 | B2 | 9/2014 | Laurin et al. |
| 8,835,654 | B2 | 9/2014 | Kong et al. |
| 9,499,480 | B2 | 11/2016 | Kong et al. |
| 2006/0079578 | A1 | 4/2006 | Laurin et al. |
| 2009/0076167 | A1 | 3/2009 | Czarnik |
| 2010/0120744 | A1 | 5/2010 | Gant |
| 2012/0214745 | A1 | 8/2012 | Naicker et al. |

FOREIGN PATENT DOCUMENTS

| JP | 2010514674 A | 5/2010 |
|---|---|---|
| WO | 1994022437 | 10/1994 |
| WO | 1996028187 | 9/1996 |
| WO | 2009019534 | 12/2009 |
| WO | 2015143447 | 9/2015 |
| WO | 2017-27582 | 3/2017 |
| WO | 2017044840 | 3/2017 |

OTHER PUBLICATIONS

Cecil Textbook of Medecine, 20th edition (1996), vol. 2, pp. 2050-2057.
Cecil Textbook of Medecine, 20th edition (1996), vol. 2., pp. 1992-1996.
FDA mulls drugs to slow late-stage Alzheimer's [online], retrieved on Sep. 23, 2003 from the Internet, URL: http://www.cnn.com/2003/HEALTH/conditions/09/24/Alzheimers.drug.ap/indexhtml.
Courtyn, J. et al., Synthesis of 11C-labelled acamprosate for PET studies., J. Labelled Cpd. Radiopharm, 2001, vol. 44, pp. 643-651.
International Search Report and Written Opinion issued in International application No. PCT/CA2018/050334 dated Jun. 1, 2018.
Zornoza, T. et al., Evidence of a flip-flop phenomenon in acamprosate pharmacokinetics: an in vivo study in rats., Biopharm. Drug Dispos., 2006, vol. 27, pp. 305-311.
Zornoza, T. et al., Disposition of Acamprosate in the Rat: Influence of Probenecid, Biopharm. Drug Dispos., 2002, vol. 23, pp. 283-291.
Saivin, S. et al., Clinical Pharmacokinetics of Acamprosate, Clin. Pharmacokinet., 1998, vol. 35, pp. 331-345.
Chabenat, C. et al., Physicochemical, pharmacological and pharmacokinetic study of a new GABAergic compound, calcium acetylhomotaurinate, Methods ans Findings in Experimental and Clinical Pharmacology, 1998, vol. 10, pp. 311-317 (Abstract only).

(Continued)

*Primary Examiner* — Shawquia Jackson
(74) *Attorney, Agent, or Firm* — BCF LLP

(57) ABSTRACT

There are provided isotope-enriched compounds of Formula (I) and pharmaceutically acceptable salts or esters thereof, as well as pharmaceutical compositions thereof and methods of use thereof for prevention and treatment of amyloid-β related diseases, such as Alzheimer's disease.

$$R^1R^2X\text{—}CR_2\text{—}CH_2\text{—}CH_2\text{—}SO_3H \quad (I)$$

17 Claims, 2 Drawing Sheets

(56) References Cited

OTHER PUBLICATIONS

Shoo, L. et al., The kinetic isotope effect in the search for deuterated drugs, Drug News & Perpectives 2010, 23(6), 398-404.
Foster, A.B., Deuteirum Isotope Effects in the Metabolism of Drugs and Xenobiotics: Implications for Drug Design, Advances in Drug Research, vol. 14, 1985.
Petition for Inter Partes Review of U.S. Pat. No. 10,472,323, Inter Partes Review No. IPR2021-00347, Dec. 18, 2020.
Exhibit 1002 for Inter Partes Review, Declaration of F. Peter Guengerich, Ph.D.
Exhibit 1010 for Inter Partes Review, P. Atkins et al., Chemical Principles, Third Edition (2005).
Exhibit 1012 for Inter Partes Review, Morgan, et al. "Old Drugs Yield New Discoveries: Examples from the Prodrug, Chiral Switch, and Site-Selective Deuteration Strategies" in Barratt and Frail, Drug Repositioning: Bringing New Life to Shelved Assets and Existing Drugs (2012).
Exhibit 1013 for Inter Partes Review, L.E. Dyck, et al., "Effects of Deuterium Substitution on the Catabolism of β-Phenylethylamine: An In Vivo Study," J. Neurochemistry, 46:2, 399-404, 399 (1986).
Exhibit 1018 for Inter Partes Review, T.R. Browne, ed., Stable Isotopes in Pharmaceutical Research (1997).
Exhibit 1019 for Inter Partes Review, V.E. Anderson, "Isotope effects on enzyme-catalyzed reactions," Current Opinion in Structural Biology, 2:757-764 (1992).
Exhibit 1020 for Inter Partes Review, C. Hennig, et al., "Secondary Kinetic Isotope Effect in Nucleophilic Substitution," J. Phys. Chem. A, 110:3071-79 (2006).
Exhibit 1022 for Inter Partes Review, J. Belleau et al., "Effect of Deuterium Substitution in Sympathomimetic Amines on Adrenergic Responses," Science 133:102-104 (1961).
Exhibit 1024 for Inter Partes Review, J. Qiu, et al., "A New Class of Conformationally Rigid Analogues of 4-Amino-5-halopentanoic Acids, Potent Inactivators of γ-Aminobutyric Acid Aminotransferase," J. Med. Chem. 43:706-720, 712 (2000).
Exhibit 1025 for Inter Partes Review, J. Mayer et al., "Homotaurine Metabolized to 3-Sulfopropanoate in Cupriavidus necator H16." J. Bacteriology, 191:6052-6058 (2009).
Exhibit 1021 for Inter Partes Review, O'Leary, "Multiple Isotope Effects on Enzyme-Catalyzed Reactions," Annu. Rev. Biochem., 58:377-401 (1989).
Exhibit 1023 for Inter Partes Review, Caldwell, J., et al., "An Introduction to Drug Disposition: the Basic Principles of Absorption, Distribution, Metabolism, and Excretion," Toxic Pathology, 23(2), 102-114, 110 (1995).
Exhibit 1026 for Inter Partes Review, T.S. Soper, et al., "Different Modes of Action of Inhibitors of Bacterial D-Amino Acid Transaminase." J. Biol. Chem., 256:4263-68 (1981).
Exhibit 1028 for Inter Partes Review, Yu et al., "Stereospecific Deuterium Substitution at the α-Carbon Position of Dopamine," Biochemical Pharmacology, 35:1027-36 (1986).
Exhibit 1031 for Inter Partes Review, Guengerich, F. P., "Kinetic deuterium isotope effects in cytochrome P450 reactions," Methods in Enzymology, vol. 596, Chap. 9, pp. 217-238 (2017).
Exhibit 1034 for Inter Partes Review, R. I. Feldman and H Weiner, "Horse Liver Aldehyde Dehydrogenase," J. Biol. Chem. 247 (1), 267-272 (1972).
Exhibit 1027 for Inter Partes Review, G. Burnett et al., "Mechanism-based Inaction of Pig Heart LAlanine Transaminase by L-Propargylglcine," J. Biol. Chem., 255:3487-3497 (1980).
Exhibit 1029 for Inter Partes Review, P.H. Yu, "Deuterium Isotope Effect in γ-Aminobutyric Acid Transamination," J. Neurochemistry, 48:440-446, 443 (1987).
Exhibit 1030 for Inter Partes Review, M.A. Rishavy, et al., "13C and 15N Kinetic Isotope Effects on the Reaction of Aspartate Aminotransferase," Biochemistry, 27:7546-51 (2000).
Exhibit 1032 Inter Partes Review, C. Walsh, Enzymatic Reaction Mechanisms, Freeman, New York, pp. 796-797, (1979).
Exhibit 1033 for Inter Partes Review, Miller et al., "Structure-Activity Relationships in the Oxidation of Para-Substituted Benzylamine Analogues by Recombinant Human Liver Monoamine Oxidase." Biochemistry 38:41, 13670-13683 (1999).
Exhibit 1035 for Inter Partes Review, B. Yoval-Sánchez et al., "New insights into the half-of-the-sites reactivity of human aldehyde dehydrogenase 1A1," Proteins 81 (8), 1330-1339 (2013).
Exhibit 1036 for Inter Partes Review, Guengerich, F. P., "Cytochrome P450 and Chemical Toxicology," Chem. Res. Toxicol. 2008, 21, 1, 70-83.
Exhibit 1037 for Inter Partes Review, Alzheon Press Release, "Alzheon Presents Positive Results of ALZ-801 Clinical Studies that Lead to Advancement to Pivotal Phase 3 Study in Alzheimer's Patients with APOE4/4" (Jul. 25, 2016).
Exhibit 1014 for Inter Partes Review, Anslyn, et al. Modern Physical Organic Chemistry (2006).
Exhibit 1011 for Inter Partes Review, CRC Handbook of Chemistry and Physics, 95th Edition (2015).

ISOTOPE-ENRICHED 3-AMINO-1-PROPANESULFONIC ACID DERIVATIVES AND USES THEREOF

CROSS-REFERENCE TO RELATED APPLICATIONS

This application is a continuation of U.S. patent application Ser. No. 15/476,255 filed Mar. 31, 2017, now U.S. Pat. No. 10,472,323 issued Nov. 12, 2019, which claims the benefit of priority to Chinese application no. 201710168819.2 filed Mar. 21, 2017, the entire contents of which are hereby incorporated by reference.

FIELD

The present disclosure relates to isotope-enriched 3-amino-1-propanesulfonic acid (3APS) and derivatives, compositions thereof, and methods of use thereof in therapeutic applications such as the prevention and treatment of Alzheimer's disease.

BACKGROUND

Alzheimer's disease (AD) is a progressive degenerative disease of the brain primarily associated with aging. Prevalence of AD in the United States in 2000 was close to 4.5 Million. It has been estimated that approximately one in ten individuals over 65 and nearly half of those over 85 are affected by AD. Approximately 360,000 patients will be diagnosed with AD each year in the United States alone.

Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease (AD) is characterized by two major pathologic observations in the brain: neurofibrillary tangles and beta amyloid (or neuritic) plaques, comprised predominantly of an aggregate of a peptide fragment known as Aβ. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders.

3-amino-1-propanesulfonic acid (also known as 3APS, Tramiprosate, and Alzhemed™) is a promising investigational product candidate for the treatment of Alzheimer's disease. 3APS was the subject of Phase III clinical trials in North America and Europe (Wright, T. M., Drugs of Today (2006), 42(5): 291-298). Results from these clinical studies have been published (Journal of Nutrition, Health & Aging (2009), 13(6), 550-557; Journal of Nutrition, Health & Aging (2009), 13(9), 808-812; Archives of Medical Science (2011), 7(1), 102-111; Journal of Alzheimer's Disease (2016), 50(3), 807-816; Aging: Clinical and Experimental Research (2012), 24(6), 580-587).

3APS is believed to act by reducing amyloid aggregation, deposition and/or load of amyloid in the brain through its binding to soluble Aβ peptide. It is known that 3APS is metabolized both in vitro and in vivo (U.S. Pat. No. 8,748,656). 3APS is extensively metabolized in vivo to produce three potential metabolites: 2-carboxyethanesulfonic acid, 3-hydroxy-1-propanesulfonic acid, and 3-acetylamino-1-propansulfonic acid. The only major metabolite of 3APS produced in mice, rats, dogs, and humans is 2-carboxyethanesulfonic acid. This metabolism of 3APS has significant effect on its pharmacokinetic profile and accordingly its pharmaceutical efficacy. In order to increase therapeutic effectiveness of 3APS, attempts have been made to increase overall bioavailability, for example by increasing stability or reducing metabolism. One such approach is the use of prodrugs and derivatives of 3APS that will generate 3APS in vivo after administration to a subject (see, for example, U.S. Pat. No. 8,748,656 and PCT International Application Publication No. WO 2015/143447, the contents of which are hereby incorporated by reference in their entirety).

Foreign substances including compounds and other therapeutic agents are often metabolized to facilitate their elimination from the body. For example, various enzymes such as cytochrome $P_{450}$ enzymes, esterases, proteases, reductases, dehydrogenases, transaminases, and monoamine oxidases, can react with foreign substances and catalyze their conversion to more polar metabolites for renal excretion. The resultant metabolites can have substantially different pharmacokinetic, pharmacodynamic, and acute and long-term toxicity profiles relative to the parent compounds.

Such metabolic reactions frequently involve the oxidation of a carbon-hydrogen bond to a carbon-oxygen or a carbon-carbon π-bond. Carbon-hydrogen bond strength is directly proportional to the absolute value of the ground-state vibrational energy of the bond. This vibrational energy depends on the mass of the atoms that form the bond and increases as the mass of one or both of the atoms making the bond increases. Since deuterium (D) has twice the mass of protium ($^1$H), a carbon-deuterium (C-D) bond is stronger than the corresponding carbon-protium (C—$^1$H) bond. If a C—$^1$H bond is broken during a rate-determining step of a metabolic reaction, then substituting a deuterium for that protium will cause a decrease in the reaction rate.

Deuterium is a stable and non-radioactive isotope of hydrogen which has approximately twice the mass of protium, which is the most common isotope of hydrogen. Deuteration of pharmaceuticals to improve pharmacokinetics and pharmacodynamics has been demonstrated previously. For example, SD-809, a deuterated drug (deutetrabenazine), has been used for the treatment of Huntington's disease. Such isotope-enrichment can potentially affect a therapeutic agent's metabolism, release from prodrugs and derivatives, absorption, and/or clearance, significantly altering the agent's pharmacokinetic profile.

SUMMARY

It is an object of the present invention to ameliorate at least some of the deficiencies present in the prior art. Embodiments of the present technology have been developed based on the inventors' appreciation that there is a need for increasing the therapeutic efficacy of 3APS, for example by increasing bioavailability, stability, and/or reducing metabolism of the compound. These and other needs can be satisfied by the disclosure herein of isotope-enriched 3-amino-1-propanesulfonic acid (3APS) derivatives and/or prodrugs, pharmaceutical compositions and uses thereof to treat various Aβ-related disorders.

In a first broad aspect, there are provided compounds of Formula I, or pharmaceutically acceptable salts or esters thereof:

$$R^1R^2X\text{—}CR_2\text{—}CH_2\text{—}CH_2\text{—}SO_3H \qquad (I)$$

where: $R^1$ and $R^2$ are independently a hydrogen of natural abundance or a protecting group that is of natural abundance or isotope-enriched, the protecting group being selected from acyl, carbonyl, thiocarbonyl, and carbamoyl groups; X is a nitrogen of natural abundance, an $^{15}$N-enriched nitrogen ($^{15}$N) or a combination thereof; and R is a hydrogen of natural abundance, a deuterium (D) or a combination thereof; provided that $R^1$, $R^2$, X and R are not all atoms of natural abundance (in other words, when $R^1$ and $R^2$ are atoms of natural abundance, X and R are not both atoms of natural abundance, i.e., R is not a hydrogen of natural abundance when X is a nitrogen of natural abundance. In other words, when $R^1$ and $R^2$ are both atoms of natural abundance or both comprise at least one atom of natural abundance, only one of X and R is an atom of natural abundance: if X is a nitrogen of natural abundance, then R is D; if R is H, then X is $^{15}$N). In some embodiments, R is a hydrogen of natural abundance and X is $^{15}$N. In some embodiments, R is D and X is a nitrogen of natural abundance. In some embodiments, R is D and X is $^{15}$N. In some embodiments, when X and R are atoms of natural abundance, $R^1$ and $R^2$ are not atoms of natural abundance or do not comprise only atoms or protecting groups of natural abundance (i.e., at least one of $R^1$ and $R^2$ is isotope-enriched). In one embodiment of Formula (I), $R^1$ is an amino acid residue with or without isotope-enrichment and $R^2$ is a hydrogen of natural abundance.

In one embodiment of Formula (I), R is a hydrogen of natural abundance; X is a nitrogen of natural abundance; and at least one atom in $R^1$ and/or $R^2$ is not of natural abundance.

In a second broad aspect, there are provided compounds of Formula II, or pharmaceutically acceptable salts or esters thereof:

where X is a nitrogen of natural abundance, an N-15 isotope-enriched nitrogen (also referred to herein as "$^{15}$N-enriched nitrogen" or "$^{15}$N") or a combination thereof, and R is a hydrogen of natural abundance, a deuterium (D) or a combination thereof, provided that X and R are not both atoms of natural abundance at the same time (in other words, R is not a hydrogen of natural abundance when X is a nitrogen of natural abundance, e.g., when X is a nitrogen of natural abundance, R is D). In some embodiments, R is a hydrogen of natural abundance and X is $^{15}$N. In some embodiments, R is D and X is a nitrogen of natural abundance. In some embodiments, R is D and X is $^{15}$N.

In a third broad aspect, there are provided compounds of Formula III, or pharmaceutically acceptable salts or esters thereof:

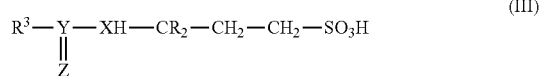

where X and R are as defined above; Y is a carbon of natural abundance, a $^{13}$C-enriched carbon ($^{13}$C) or a combination thereof; Z is a sulfur, an oxygen of natural abundance, an $^{18}$O-enriched oxygen ($^{18}$O), an $^{17}$O-enriched oxygen ($^{17}$O) or a combination thereof; and $R^3$ is a substituting group selected from substituted or unsubstituted alkyl, aryl, amino alkyl, amino arylalkyl, heterocyclyl, alkoxyl, alkylthio, alkylamino, acyloxyl, and thioacyloxyl; provided that at least one of X, R, Y and Z is not an atom of natural abundance. In some embodiments, R is not a hydrogen of natural abundance when X is a nitrogen of natural abundance.

In one embodiment of Formula (III), $R^3$, Y, and Z taken together form an acyl group connected to X, forming an amide bond linkage. In another embodiment, $R^3$ is an amino acid residue and $R^3$, Y, and Z taken together form an acyl group connected to X, the acyl group being derived from an amino acid. The amino acid may be an L-amino acid, a D-amino acid, or a mixture of L and D forms. The amino acid may be a natural or an unnatural amino acid. In a particular embodiment, the amino acid is an L-amino acid. In an embodiment, the amino acid is a naturally-occurring L-amino acid.

In some embodiments, there are provided compounds of Formulae IV and V, or pharmaceutically acceptable salts or esters thereof:

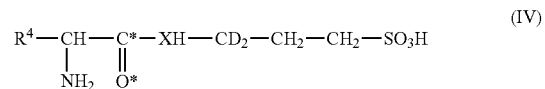

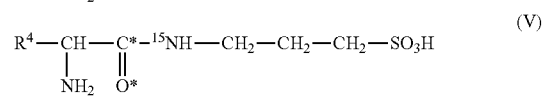

where $R^4$ is a side chain of a natural or unnatural amino acid; O* is an oxygen atom of natural abundance, an $^{18}$O-enriched oxygen ($^{18}$O), an $^{17}$O-enriched oxygen ($^{17}$O) or a combination thereof; and C* is a carbon atom of natural abundance, a $^{13}$C-enriched carbon ($^{13}$C) or a combination thereof. The corresponding amino acid may be an L-amino acid, a D-amino acid, or a mixture of L and D forms. The corresponding amino acid may be a natural or an unnatural amino acid.

In another embodiment, there are provided compounds of Formula VI, or pharmaceutically acceptable salts or esters thereof:

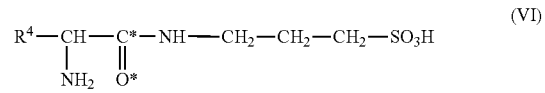

where $R^4$ is a side chain of a natural or unnatural amino acid; $O^{\#}$ is an oxygen atom of natural abundance, an $^{18}$O-enriched oxygen ($^{18}$O), an $^{17}$O-enriched oxygen ($^{17}$O) or a combination thereof; and $C^{\#}$ is a carbon atom of natural abundance, a $^{13}$C-enriched carbon or a combination thereof; provided that $O^{\#}$ and $C^{\#}$ are not both atoms of natural abundance (in other words, at least one of $O^{\#}$ and $C^{\#}$ is an isotope-enriched atom, or at least one of $O^{\#}$ and $C^{\#}$ is not an atom of natural abundance). The corresponding amino acid may be an L-amino acid, a D-amino acid, or a mixture of L and D forms. The corresponding amino acid may be a natural or unnatural amino acid.

Compounds in which all the atoms or elements in the structure are in their natural abundance (non-isotope enriched compounds) are not encompassed by the present invention.

In some embodiments, the compound of Formula (I), (III), (IV), (V), or (VI) is not N-acetyl-3-amino-1-propane-sulfonic acid.

Compounds provided herein, e.g., compounds of Formula (I), (II), (III), (IV), (V), or (VI), may be enriched for one or more isotope. Any stable or pharmaceutically acceptable isotope may be used to enrich a compound of the invention. For example, an isotope-enriched compound may comprise D ($^2$H), $^{13}$C, $^{15}$N, $^{17}$O, and/or $^{18}$O.

In some embodiments, the isotope-enriched compound of Formula (I), (II), (III), (IV), (V), or (VI) is a compound shown in Table 1, Table 2, Table 3, or Table 4, or a pharmaceutically-acceptable salt, ester, chelator, hydrate, solvate, stereoisomer, or polymorphic form thereof.

TABLE 1

3,3-Dideuterium-3-amino-1-propanesulfonic acid, $^{15}$N-3-amino-1-propanesulfonic acid and selected derivatives.

| No. | Structure |
| --- | --- |
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |

TABLE 1-continued 3,3-Dideuterium-3-amino-1-propanesulfonic acid, $^{15}$N-3-amino-1-propanesulfonic acid and selected derivatives.

| No. | Structure |
| --- | --- |
| 10 | [structure] |
| 11 | [structure] |
| 12 | [structure] |

TABLE 2

Examples of N-($^{18}$O- and $^{17}$O-aminoacylated) 3-amino-1-propanesulfonic acid prodrugs.

| No. | Structure |
| --- | --- |
| 13 | [structure] |
| 14 | [structure] |
| 15 | [structure] |
| 16 | [structure] |
| 17 | [structure] |

TABLE 2-continued

Examples of N-($^{18}$O- and $^{17}$O-aminoacylated) 3-amino-1-propanesulfonic acid prodrugs.

| No. | Structure |
|---|---|
| 18 | Alanine with $^{17}$O amide linked to propanesulfonic acid |
| 19 | Serine with $^{17}$O amide linked to propanesulfonic acid |
| 20 | Valine with $^{17}$O amide linked to propanesulfonic acid |
| 21 | Phenylalanine with $^{17}$O amide linked to propanesulfonic acid |
| 22 | Histidine with $^{17}$O amide linked to propanesulfonic acid |

TABLE 3

Examples of N-(1-$^{13}$C-aminoacyl)-3-amino-1-propanesulfonic acid prodrugs and selected isotope-enriched prodrugs.

| No. | Structure |
|---|---|
| 23 | Alanine with $^{13}$C amide linked to propanesulfonic acid |
| 24 | Serine with $^{13}$C amide linked to propanesulfonic acid |
| 25 | Valine with $^{13}$C amide linked to propanesulfonic acid |
| 26 | Phenylalanine with $^{13}$C amide linked to propanesulfonic acid |
| 27 | Histidine with $^{13}$C amide linked to propanesulfonic acid |
| 28 | Valine with $^{13}$C amide linked to D$_2$-propanesulfonic acid |
| 29 | Valine with $^{18}$O amide linked to D$_2$-propanesulfonic acid |
| 30 | Valine with $^{17}$O amide linked to D$_2$-propanesulfonic acid |
| 31 | Valine with $^{18}$O, $^{13}$C amide linked to D$_2$-propanesulfonic acid |
| 32 | Valine with $^{18}$O amide linked to $^{15}$N-propanesulfonic acid |

TABLE 4

Examples of isotope-enriched 3-(histidylamino)-1-propanesulfonic acid.

| No. | Structure |
|---|---|
| 33 | Cysteine amide linked to D$_2$-propanesulfonic acid |
| 34 | Cysteine amide linked to $^{15}$N-propanesulfonic acid |

TABLE 4-continued

Examples of isotope-enriched 3-(histidylamino)-1-propanesulfonic acid.

| No. | Structure |
|---|---|
| 35 | HS-CH2-CH(NH2)-$^{13}$C(=O)-NH-CH2CH2CH2-SO3H |
| 36 | HS-CH2-CH(NH2)-C(=$^{18}$O)-NH-CH2CH2CH2-SO3H |
| 37 | HS-CH2-CH(NH2)-C(=$^{17}$O)-NH-CH2CH2CH2-SO3H |
| 38 | HS-CH2-CH(NH2)-C(=$^{18}$O)-NH-CD2-CH2CH2-SO3H |
| 39 | HS-CH2-CH(NH2)-C(=$^{18}$O)-$^{15}$NH-CH2CH2CH2-SO3H |
| 40 | HS-CH2-CH(NH2)-$^{13}$C(=O)-NH-CD2-CH2CH2-SO3H |
| 41 | HS-CH2-CH(NH2)-$^{13}$C(=O)-$^{15}$NH-CH2CH2CH2-SO3H |
| 42 | HS-CH2-CH(NH2)-$^{13}$C(=$^{18}$O)-NH-CD2-CH2CH2-SO3H |

In an embodiment, the isotope-enriched compound is 3-(acylamino)-3,3-dideuterium-1-propanesulfonic acid or 3-(acyl($^{15}$N-amino))-1-propanesulfonic acid, where the acyl group is selected from arginyl, aspartyl, asparigyl, cystyl, glutamyl, glutaminyl, glycyl, isoleucyl, leucyl, lysyl, methionyl, prolyl, selenocystyl, threonyl, tryptophanyl, tyrosyl, and 4-hydroxyisoleucyl; or a pharmaceutically-acceptable salt, ester, chelator, hydrate, solvate, stereoisomer, or polymorphic form thereof.

In another embodiment, the isotope-enriched compound is 3-((1-$^{13}$C-acyl)amino)-1-propanesulfonic acid, 3-((1-$^{18}$O-acyl)amino)-1-propanesulfonic acid, or 3-((1-$^{17}$O-acyl)amino)-1-propanesulfonic acid, where the acyl group is selected from arginyl, aspartyl, asparigyl, cystyl, glutamyl, glutaminyl, glycyl, isoleucyl, leucyl, lysyl, methionyl, prolyl, selenocystyl, threonyl, tryptophanyl, tyrosyl, and 4-hydroxyisoleucyl; or a pharmaceutically-acceptable salt, ester, chelator, hydrate, solvate, stereoisomer, or polymorphic form thereof.

In some embodiments, the compounds of the present invention are in their original acid or base forms, such as amino sulfonic acid. In other embodiments, the compounds of the present invention encompass other pharmaceutically accepted forms or the original form, such as inorganic salt, organic salt, ester, chelator, hydrate, or solvate. The invention also encompasses different polymorphic forms of compounds according to Formulae I to VI and Tables 1-4.

Without wishing to be limited by theory, it is believed that isotope-enriched derivatives and/or prodrugs of SAPS provided herein can improve therapeutic efficacy of 3APS by improving its therapeutic bio-distribution and/or pharmacokinetic profiles, for example by increasing bioavailability of the compound, reducing metabolism of the compound, increasing compound stability, and/or changing the release rate of 3APS from a prodrug.

According to another broad aspect, there are provided methods for increasing the therapeutic effectiveness of 3APS comprising administering to a subject, preferably a human subject, an effective amount of an isotope-enriched 3APS derivative as described herein, or a prodrug that releases an isotope-enriched 3APS derivative in the subject.

In some embodiments of methods provided herein, the compound is a compound of any one of Formulae (I)-(VI) as described herein, or a pharmaceutically acceptable salt thereof. In some embodiments of methods provided herein, the compound is a compound of any one of Formulae (I)-(VI) as described herein, or a pharmaceutically acceptable salt thereof, wherein the compound is not N-acetyl-3-amino-1-propanesulfonic acid.

According to an aspect, there are provided compounds and compositions that will yield or generate 3APS or isotope-enriched 3APS after administration to a subject. Such compounds, pharmaceutical compositions containing such compounds, and methods employing such compounds and compositions in the treatment of various amyloid-β related diseases and conditions such as Alzheimer's disease are provided herein.

In another broad aspect, there are provided pharmaceutical compositions comprising a compound described herein, or a pharmaceutically acceptable salt thereof, and a pharmaceutically acceptable carrier. In some embodiments, there are provided pharmaceutical compositions comprising a compound of any one of Formulae I-VI, or a pharmaceutically acceptable salt thereof, and a pharmaceutically acceptable carrier. In some embodiments, there are provided pharmaceutical compositions comprising a compound of any one of Formulae I-VI, or a pharmaceutically acceptable salt thereof, and a pharmaceutically acceptable carrier, wherein the compound is not N-acetyl-3-amino-1-propanesulfonic acid.

In some embodiments, compounds of Formulae (I)-(VI) can act to increase the therapeutic effectiveness of 3APS in a subject, as compared to administration of 3APS that is not isotope-enriched (i.e., in which all the atoms in the 3APS compound are in their natural abundance). In some embodiments, compounds of Formulae (I)-(VI) can act to increase the bioavailability of 3APS, the AUC of 3APS, the brain levels of 3APS, the CSF levels of 3APS, the $C_{max}$ of 3APS, the $T_{max}$ of 3APS, the stability of 3APS, the therapeutic bio-distribution of 3APS, and/or the bioabsorption of 3APS in a subject, as compared to administration of 3APS that is not isotope-enriched. In some embodiments, the effective therapeutic level of 3APS in a selected human tissue such as brain or CSF is increased after administration of a compound of any of Formulae (I)-(VI), as compared to administration of 3APS that is not isotope-enriched. In some embodiments, compounds of Formulae (I)-(VI) can act to reduce the metabolism of 3APS in a subject, as compared to administration of 3APS that is not isotope-enriched. In some embodiments, compounds of Formulae (I)-(VI) can act to reduce the side effects of 3APS in a subject, as compared to administration of 3APS that is not isotope-enriched.

In some embodiments, compounds of Formulae (I)-(VI) and compositions thereof are used to prevent or treat an amyloid-β related disease or condition such as Alzheimer's disease in a subject. In some embodiments, compounds of Formulae (I)-(VI) inhibit amyloid-β deposition, oligomerization, and/or toxicity, and/or improve clinical parameters associated with an amlyoid-β related disease or condition (such as performance on cognitive tests).

In some embodiments, administration of compounds and compositions of the invention may improve the therapeutic bio-distribution of 3APS in the subject as compared to administration of the same equivalent molar dose of non-isotope enriched 3APS or a non-isotope enriched prodrug of 3APS. For example, the bioavailability of 3APS may be improved, the stability of 3APS may be improved, the metabolism of 3APS may be reduced, or the release rate of 3APS from a prodrug may be improved, as compared to administration of the same equivalent molar dose of non-isotope enriched 3APS or a non-isotope enriched prodrug of 3APS. In an embodiment, the oral AUC of 3APS in the subject is improved (e.g., increased by at least about 2%, about 5%, about 10%, or about 20%), as compared to the oral AUC after administration of the same equivalent molar dose of non-isotope enriched 3APS or a non-isotope enriched prodrug of 3APS.

In a further aspect, there are provided kits for treating an amyloid-β related disease in a subject in need thereof, comprising a compound (or a pharmaceutically acceptable salt thereof) or a pharmaceutical composition, as described herein; optionally one or more additional component such as acids, bases, buffering agents, inorganic salts, solvents, antioxidants, preservatives, or metal chelators; and instructions for use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
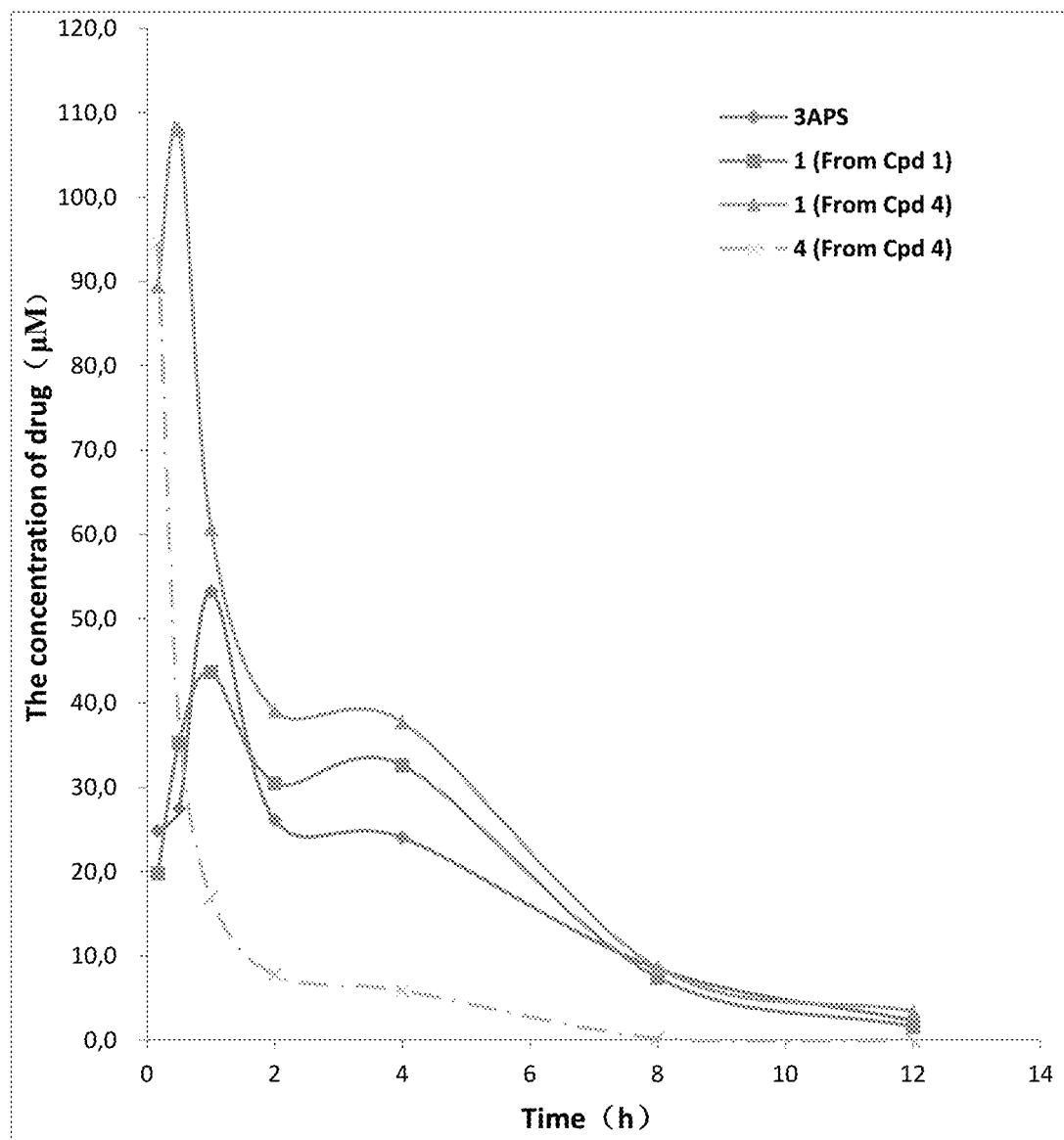
FIG. 1 shows plasma concentration—time curves of the compound following an oral administration of 3APS (non-isotope enriched), compound 1, and compound 4, including the concentration-time curve of compound 4 in the same experiment. Curves labeled with -♦-, -■-, and -▲- represent plasma drug concentration following administration of 3APS (of natural abundance), compound 1 and compound 4, respectively; and the curve labeled with -x- represents plasma prodrug concentration following administration of compound 4. The figure shows that at the mole-equivalent oral dose, the isotope-enriched compound 1 had a delayed metabolic profile and an improved exposure compared to 3APS, while compound 4 demonstrated even greater improvement of drug exposure.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "acyclic" refers to an organic moiety without a ring system. The term "aliphatic group" includes organic moieties characterized by straight or branched-chains, typically having between 1 and 15 carbon atoms. Aliphatic groups include non-cyclic alkyl groups, alkenyl groups, and alkynyl groups.

As used herein, the term "alkenyl" refers to unsaturated hydrocarbons having from two to twelve carbon atoms, including linear, branched, and cyclic non aromatic alkenyl groups, and comprising between one to six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The term "$C_2$-$C_n$alkenyl", wherein n is an integer from 3 to 12, refers to an alkenyl group having from 2 to the indicated "n" number of carbon atoms.

As used herein, the term "alkynyl" refers to unsaturated hydrocarbons having from two to twelve carbon atoms, including linear, branched, and cyclic non aromatic alkynyl groups, and comprising between one to six carbon-carbon triple bonds. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl", wherein n is an integer from 3 to 12, refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal or less than 8 carbon atoms in their ring structure.

The terms "aryl" and "aryl ring" refer to aromatic groups having "4n+2".pi.(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to an heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein means an amine group having respectively one and at least two $C_1$-$C_6$alkyl groups attached thereto. The term "arylamino" and "diarylamino" include groups wherein the nitrogen is bound to at least one or two aryl groups, respectively. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —$NO_2$; the terms "halo" and "halogen" refer to bromine, chlorine, fluorine or iodine substituents; the term "thiol", "thio", or "mercapto" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as perhalogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_6$alkyl, $C_1$-$C_6$alkenyl, $C_1$-$C_6$alkynyl, e.g., acetyl), a cycloalkyl group ($C_3$-$C_8$cycloalkyl), a heterocyclic group ($C_3$-$C_8$heterocycloalkyl and $C_5$-$C_6$heteroaryl), an aromatic group ($C_6$aryl, e.g., benzoyl), and the like. Acyl groups may be unsubstituted or substituted acyl groups (e.g. salicyloyl).

It should be understood that "substitution" or "substituted with" includes the implicit proviso that such substitution is in accordance with the permitted valence of the substituted atom and the substituent, and that the substitution results in a stable compound, i.e., a compound which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g., if the group contains an alkyl group, an aryl group, or other.

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

The terms "Abeta", "Aβ", "β-amyloid", and "amyloid-β" are used interchangeably herein to refer to any peptide resulting from beta-secretase mediated cleavage of Amyloid Precursor Protein (APP), including for example peptides of 37, 38, 39, 40, 41, 42, and 43 amino acids, and extending from the beta-secretase cleavage site to amino acids 37, 38, 39, 40, 41, 42, or 43. Other forms of the above peptides are also included, e.g., N-terminal truncated species such as pyroglutamic forms pE3-40, pE3-42, pE3-43, pE11-42, pE11-43, and the like. For convenience of nomenclature, "$A\beta_{1-42}$" may be referred to herein as "Aβ(1-42)" or simply as "$A\beta_{42}$" (and likewise for any other amyloid peptides discussed herein). As used herein, the terms "Abeta", "Aβ", "β-amyloid", and "amyloid-β" are synonymous, referring collectively to truncated and non-truncated peptide species of the sequence between β- and γ-cleavage sites of APP.

The terms "amyloid-β disease" and "amyloid-β related disease" are used to refer to a variety of diseases and conditions associated with amyloid-β, including, without limitation, mild cognitive impairment (MCI); vascular dementia; early-onset Alzheimer's disease; Alzheimer's disease, including sporadic (non-hereditary) Alzheimer's disease and familial (hereditary) Alzheimer's disease; age-related cognitive decline; cerebral amyloid angiopathy (CAA); hereditary cerebral hemorrhage; senile dementia; Down's syndrome; degenerative dementia; dementia or mixed vascular and degenerative origin; dementia associated with Parkinson's disease; dementia associated with progressive supranuclear palsy; dementia associated with cortical basal degeneration; dementia associated with diffuse Lewy body type of Alzheimer's disease; inclusion body myositis (IBM); and age-related macular degeneration (ARMD).

As used herein, "AUC" refers to the area under a curve representing the concentration of a compound in a biological sample from a subject as a function of time following administration of the compound to the subject. Non-limiting examples of such biological samples include biological fluids such as plasma, blood, cerebrospinal fluid (CSF), and saliva; organ homogenates such as brain and liver homogenates; and the like. The AUC can be determined by measuring the concentration of a compound in a biological sample such as the plasma, blood, CSF or brain homogenate using methods such as liquid chromatography-tandem mass spectrometry (LC/MS/MS), at various time intervals, and calculating the area under the concentration-versus-time curve. Suitable methods for calculating the AUC from a drug concentration-versus-time curve are well known in the art. As relevant to the disclosure here, an AUC for 3APS can be determined by measuring the concentration of 3APS in the plasma, blood, CSF or brain homogenate of a subject following oral administration of a compound described herein to the subject.

"Bioavailability" refers to the rate and amount of a compound that reaches the systemic circulation of a subject following administration of the compound or a prodrug thereof to the subject and can be determined by evaluating, for example, the plasma or blood concentration-versus-time profile for the compound. Parameters useful in characterizing a plasma or blood concentration-versus-time curve include the area under the curve (AUC), the time to peak concentration ($T_{max}$), and the maximum compound concentration ($C_{max}$). "$C_{max}$" is the maximum concentration of a compound in the biological sample of a subject following administration of a dose of the compound to the subject. "$T_{max}$" is the time to the maximum concentration ($C_{max}$) of a compound in the biological sample of a subject following administration of a dose of the compound to the subject. Bioavailability is often expressed as F (%) referring to the ratio in percentage of the AUC of the compound for a specific mode of administration (e.g., orally) over AUC of the compound after intravenous (IV) administration.

"Bioequivalence" refers to equivalence of the rate and extent of absorption of a therapeutic agent, such as a compound, after administration of equal doses of the agent to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, or AUC.

As used herein the term "effective amount" refers to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

As used herein, the term "therapeutic bio-distribution of 3APS" refers to one or more pharmacokinetic parameters of 3APS which affect 3APS therapeutic activity. Examples of such pharmacokinetic (PK) parameters include, but are not limited to: bioavailability of 3APS, AUC of 3APS, brain levels of 3APS, CSF levels of 3APS, $C_{max}$ of 3APS, $T_{max}$ of 3APS, and/or bio-absorption of 3APS, etc.

In some embodiments, therapeutic efficacy of 3APS may be increased by increasing therapeutic bio-distribution of 3APS, e.g., increasing bioavailability of 3APS, increasing stability of 3APS, reducing metabolism of 3APS, and/or increasing other pharmacokinetic parameters of 3APS after administration, as compared to administration of non-isotope enriched 3APS or prodrugs thereof.

As used herein, the terms "increased (or like terms, e.g., increasing, increase in, etc.) therapeutic effectiveness/efficacy of 3APS" and "enhanced (or like terms, e.g., enhancing, enhancement, etc.) therapeutic effectiveness/efficacy of 3APS" refer to an increased effectiveness of 3APS as measured, e.g., by one or more parameters listed under "therapeutic bio-distribution of 3APS" above, e.g., by 5%, 10%, 20%, 30%, 40%, 50%, 60%, 70%, 80%, 90%, 95%, 99%, 125%, etc., or even more, e.g., 2, or 4 fold, or even more when administered to a subject, e.g., animal or human, which increase is with respect to the same equivalent molar dose of non-isotope enriched 3APS. In some embodiments, such % increases are achieved also with respect to 3APS administered orally in the formulation of Table 3 of U.S. Application Publication No. 2006-0079578, published Apr. 13, 2016. Effectiveness can also be as measured, for example, by effect on characteristics of a disease such as Alzheimer's disease, e.g., by the reduction of plaques or AD load in the brain, or by an improvement in selected manifestations of the disease, e.g., memory loss, cognition, reasoning, judgment, orientation, etc. Such effects may be measured using cognitive tests such as ADAS-COG, MMSE, CDR, and the like. See U.S. Application Publication No. 2006-0079578, published Apr. 13, 2016, for details on how to measure effects on characteristics of such diseases.

The term "lessening metabolism of 3APS" (or related terms such as reduction, less, lowering, reducing, lowered, etc) refers to decreasing the degree or amount of metabolism of 3APS, e.g., first-pass metabolism in the GI tract or liver of 3APS, by e.g., 5%, 10%, 20%, 30%, 40%, 50%, 60%, 70%, 80%, 90%, 95%, 99%, or even 100%, which decrease is with respect to the degree or amount of metabolism of 3APS that occurs when the same equivalent molar dose of non-isotope enriched 3APS is administered. In some embodiments, such % decreases may be achieved also with respect to 3APS administered orally in the formulation of Table 3 of U.S. Application Publication No. 2006-0079578, published Apr. 13, 2016.

The term "reduction of side effects of 3APS" refers to decreasing the amount of or severity of one or more side effects of 3APS by, e.g., 5%, 10%, 20%, 30%, 40%, 50%, 60%, 70%, 80%, 90%, 95%, 99%, or 99.9%, or even 100%, which decrease is with respect to the amount of or severity of a side effect of 3APS that is exhibited when the same equivalent molar dose of non-isotope enriched 3APS is administered. In some embodiments such % decreases are achieved also with respect to 3APS administered orally in the formulations of Table 3 of U.S. Application Publication No. 2006-0079578, published Apr. 13, 2016. More generally, the terms lessening etc., increasing etc., refer in context herein to the percentage changes, e.g., by 5%, 10%, 20%, 30%, 40%, 50%, 60%, 70%, 80%, 90%, 95%, 99%, 125%, etc., or even more, e.g., 2, or 4 fold, or even more.

In some embodiments, AUC of 3APS is increased by at least about 20% by administration of a compound of the present invention as compared to administration of the same equivalent molar dose of non-isotope enriched 3APS or a prodrug thereof. In some embodiments, oral AUC of 3APS is increased by at least about 20% by administration of a compound of the present invention as compared to oral administration of the same equivalent molar dose of non-isotope enriched 3APS or a prodrug thereof. In other embodiments, AUC is increased by at least about 5%, at least about 10%, at least about 25%, at least about 30%, or at least about 40%.

The contents of U.S. Application Publication No. 2006-0079578, published Apr. 13, 2016, are incorporated herein by reference in their entirety, including the pharmacokinetic data therein (such as the data in Example 1 and Table 3 therein) for providing inter alia a comparative basis for the effects achieved by administration of compounds provided herein.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, or carrier with which a compound is administered.

"Pharmaceutical composition" refers to at least one compound and at least one pharmaceutically acceptable vehicle, with which the compound is administered to a patient.

"Preventing" or "prevention" is intended to refer at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, DAD, ADAS-Cog, or another test known in the art. For example, the methods of the invention may successfully treat a subject's dementia by slowing the rate of or lessening the extent of cognitive decline.

"Therapeutically effective amount" means the amount of compound that, when administered to a patient for treating or preventing a disease, is sufficient to effect such treatment or prevention of the disease. The "therapeutically effective amount" will vary depending on the compound, the disease and its severity, and the age, weight, etc., of the patient having the disease to be treated or prevented.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of the protease) or the pharmacokinetics for a particular agent. A wide variety of groups have been used to modify compounds to form prodrugs, for example, esters, ethers, phosphates, etc. When the prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the parent drug.

The term "ester" refers to compounds that can be represented by the formula RCOOR (carboxylic ester) or the formula $RSO_3R'$ (sulfonate ester), where the group R can be, for example SAPS or the 3-aminopropane part thereof, and the group R' can be another organic group. These compounds are usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Be), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), 2-aminopimelic acid (Apm), biphenylalanine (Bip), para-bromophenylalanine (4-Br-Phe), ortho-chlorophenylalanine (2-$C_1$-Phe), meta-chlorophenylalanine (3-Cl-Phe), para-chlorophenylalanine (4-$C_1$-Phe), meta-chlorotyrosine (3-$C_1$-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-$C_{1\text{-}2}$-Phe), 3,4-difluororphenylalanine (3,4-$F_2$-Phe), 3,5-diiodotyrosine (3,5-$I_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), paraiodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

Where multiple substituents are indicated as being attached to a structure, it is to be understood that the substituents can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

Isotope-Enriched Compounds

Isotopic enrichment is a process by which the relative abundance of the isotopes of a given element are altered, thus producing a form of the element that has been enriched (i.e., increased) in one particular isotope and reduced or depleted in its other isotopic forms. As used herein, an "isotope-enriched" compound or derivative refers to a compound in which one or more specific isotopic form has been increased, i.e., one or more of the elements has been enriched (i.e., increased) in one or more particular isotope. Generally, in an isotope-enriched compound or derivative, a specific isotopic form of an element at a specific position of the compound is increased. It should be understood however that isotopic forms of two or more elements in the compound may be increased. Further, an isotope-enriched compound may be a mixture of isotope-enriched forms that are enriched for more than one particular isotope, more than one element, or both.

Under normal conditions, the natural abundances for deuterium (D or $^2H$) (a stable isotope of hydrogen with a mass approximately twice that of the usual isotope), nitrogen-15 ($^{15}N$), carbon-13 ($^{13}C$), oxygen-18 ($^{18}O$), and oxygen-17 ($^{17}O$) are 0.016%, 0.37%, 1.11%, 0.204%, and 0.037%, respectively. As used herein, an "isotope-enriched" compound or derivative possesses a level of an isotopic form that is higher than the natural abundance of that form. The level of isotope-enrichment will vary depending on the natural abundance of a specific isotopic form. In some embodiments, the level of isotope-enrichment for a compound, or for an element in a compound, may be from about 2 to about 100 molar percent (%), e.g., about 2%, about 5%, about 17%, about 30%, about 51%, about 83%, about 90%, about 95%, about 96%, about 97%, about 98%, greater than about 98%, about 99%, or 100%. In one embodiment, the level of isotope-enrichment in an isotope-enriched compound of the invention (e.g., 3APS, a compound of any of Formulae (I)-(VI), etc.) is about 5% or higher, or about 10% or higher. In another embodiment, the level of isotope-enrichment in an isotope-enriched compound of the invention (e.g., 3APS, a compound of any of Formulae (I)-(VI), etc.) is about 20% or higher, or about 50% or higher. In yet another embodiment, the level of isotope-enrichment in an isotope-enriched compound of the invention (e.g., 3APS, a compound of any of Formulae (I)-(VI), etc.) is about 75% or higher, or about 90% or higher. In still another embodiment, the level of isotope-enrichment in an isotope-enriched compound of the invention (e.g., 3APS, a compound of any of Formulae (I)-(VI), etc.) is about 95% or higher, or 100%. It should be understood that the level of isotope-enrichment for a particular compound, or a particular element of a compound, will be selected based on several properties of the compound such as its chemical, pharmacokinetic, and therapeutic profiles, with the aim of improving the compound's therapeutic efficacy, therapeutic bio-distribution, bioavailability, metabolism, stability, and/or pharmacokinetic profile.

As used herein, an "element of natural abundance" and an "atom of natural abundance" refers to the element or atom respectively having the atomic mass most abundantly found in nature. For example, hydrogen of natural abundance is $^1H$ (protium); nitrogen of natural abundance is $^{14}N$; oxygen of natural abundance is $^{16}O$; carbon of natural abundance is $^{12}C$; and so on. A "non-isotope enriched" compound is a compound in which all the atoms or elements in the compound are isotopes of natural abundance, i.e., all the atoms or elements have the atomic mass most abundantly found in nature. This is in contrast to an isotope-enriched compound in which one or more element is enriched for one or more specific isotopic form that is not the isotope of natural abundance. Non-isotope enriched compounds are excluded from compounds of the present invention provided herein.

As used herein, the terms "Compounds of the present invention", "Compounds of the invention", and equivalent expressions refers to isotope-enriched compounds provided herein as being useful for at least one purpose of the invention, e.g., those encompassed by structural Formulae such as (I), (II), (III), (IV), (V), and (VI), and includes specific compounds mentioned herein such as those in Tables 1-4 as well as their pharmaceutically acceptable salts, esters, chelates, hydrates, and solvates.

Embodiments herein may exclude one or more of the compounds of the invention. In some embodiments, N-acetyl-3-amino-1-propanesulfonic acid is excluded from compounds of the invention.

As would be understood by a person of ordinary skill in the art, the recitation of "a compound" is intended to include salts, esters, solvates, hydrates, oxides, and inclusion complexes of that compound as well as any stereoisomeric form or polymorphic form, or a mixture of any such forms of that compound in any ratio. Thus, in accordance with some embodiments of the invention, a compound as described herein, including in the contexts of pharmaceutical compositions and methods of treatment is provided as the salt form.

It should be understood that compounds described herein may contain one or more chiral centers and/or double bonds and therefore, may exist as stereoisomers, such as double-bond isomers (i.e., geometric isomers), enantiomers, or diastereomers. Chemical structures disclosed herein are intended to encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. The chemical structures depicted herein are also intended to encompass all possible tautomeric forms of the illustrated compounds.

Compounds may exist in unsolvated forms as well as solvated forms, including hydrated forms. In general, compounds may be hydrated or solvated. Certain compounds may exist in multiple crystalline or amorphous forms. In general, all physical forms are intended to be encompassed herein.

The term "3APS" is used herein to refer to 3-amino-1-propanesulfonic acid, which is also known by alternate names including tramiprosate, Alzhemed™, and homotaurine, in which one or more atoms in the compound may or may not be in isotope-enriched form. "3APS" as used herein refers to any compound having the same structure regardless of how many or which atoms are in isotope-enriched form. For example, "3APS" is used herein to refer to compound 1 and compound 7 among the examples of the present invention.

Compounds described herein include, but are not limited to, their optical isomers, racemates, and other mixtures thereof. In those situations, the single enantiomers or diastereomer, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all tautomeric forms and crystal forms of the compound.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc,) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Compositions

In an embodiment, there is provided a pharmaceutical composition comprising a compound of the invention, e.g., a compound of any one of Formulae (I)-(VI), or a pharmaceutically acceptable salt, ester, or solvate thereof, and a pharmaceutically acceptable carrier. In an embodiment, there is provided a pharmaceutical composition comprising a compound in any one of Tables 1-4, or a pharmaceutically acceptable salt thereof, and a pharmaceutically acceptable carrier. In another embodiment, there is provided a pharmaceutical composition comprising a compound of any one of Formulae (I)-(VI) or a compound in any one of Tables 1-4, or a pharmaceutically acceptable salt thereof, and a pharmaceutically acceptable carrier, with the proviso that the compound is not N-acetyl-3-amino-1-propanesulfonic acid.

The preparation of pharmaceutical compositions can be carried out as known in the art (see, for example, Remington: The Science and Practice of Pharmacy, $20^{th}$ Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of a subject, e.g., humans and animals, without undue toxicity, irritation, allergic response, and the like, and are commensurate with a reasonable benefit/risk ratio.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier may be suitable for intravenous, intraperitoneal, intramuscular, sublingual or oral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated. Supplementary active compounds can also be incorporated into the compositions. For example, a pharmaceutical composition provided herein may further comprise at least one additional Alzheimer's disease therapeutic, as discussed below.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

In some embodiments, pharmaceutical compositions provided herein are suitable for oral administration. For example, a pharmaceutical composition may be in the form of a hard shell gelatin capsule, a soft shell gelatin capsule, a cachet, a pill, a tablet, a lozenge, a powder, a granule, a pellet, a pastille, or a dragee. Alternatively, a pharmaceutical composition may be in the form of a solution, an aqueous liquid suspension, a non-aqueous liquid suspension, an oil-in-water liquid emulsion, a water-in-oil liquid emulsion, an elixir, or a syrup. Pharmaceutical compositions may or may not be enteric coated. In some embodiments, pharmaceutical compositions are formulated for controlled release, such as delayed or extended release.

In further embodiments, compounds and compositions thereof may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets.

Tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropyl methylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (LI 00, S I 00, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K. K.

Representative examples of useful water-insoluble polymers include ethylcellulose, polyvinyl acetate (for example, Kollicoat SR #30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a compound of Formulae (I)-(VI) provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of an amyloid-β related disease. Dosages are discussed further below.

In some embodiments, there are provided pharmaceutical compositions that comprise an effective amount of a compound and/or composition described herein, and a pharmaceutically acceptable carrier. In an embodiment, there are provided pharmaceutical compositions for the treatment or prevention of an amyloid-β related disease, comprising a compound described herein, or a pharmaceutically acceptable salt thereof, and a pharmaceutically acceptable carrier. In another embodiment, there is provided a pharmaceutical composition for the prevention or treatment of an amyloid-β related disease such as Alzheimer's disease, the composition comprising a compound described herein, or a pharmaceutically acceptable salt thereof, and a pharmaceutically acceptable carrier.

Methods of Use of Compounds and Compositions

In another aspect, there are provided methods for prevention or treatment of an amyloid-β related disease in a subject by administering an effective amount of a compound or composition described herein. In a related aspect, there are provided methods for prevention or treatment of an amyloid-β related disease in a subject in need thereof by administering an effective amount of a compound or composition described herein.

The term "subject" includes living organisms with an amyloid-β related disease, or who are susceptible to or at risk of an amyloid-β related disese, e.g., due to a genetic predisposition or mutation. Examples of subjects include humans, monkeys, cows, rabbits, sheep, goats, pigs, dogs, cats, rats, mice, and transgenic species thereof. The term "subject" generally includes animals susceptible to states characterized by an amyloid-β related disease, e.g., mammals, e.g. primates, e.g. humans. The animal can also be an animal model for a disorder, e.g., a transgenic mouse model, and the like.

In some embodiments, a subject is in need of treatment by the methods provided herein, and is selected for treatment based on this need. A subject in need of treatment is art-recognized, and includes subjects that have been identified as having a disease or condition (e.g., mild cognitive impairment (MCI), Alzheimer's disease, dementia, etc.), or having a symptom of such a disease or condition, or being at risk of such a disease or condition, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

In some embodiments, a subject is an ApoE4+ (also referred to herein as "ApoE4 positive" or simply "ApoE4") subject, i.e., a subject having at least one ε4 allele of the apolipoprotein E (ApoE) gene. An ApoE4 positive subject may carry one or two copies of the ApoE4 allele. The ε4 allele of apolipoprotein E gene is the strongest genetic risk factor for patients with late-onset Alzheimer' s disease (AD). ApoE4+ subjects with at least one ε4 allele account for 50%-60% of AD cases vs. 25% prevalence in healthy individuals. ApoE4+AD patients present with decreased age of onset, increased severity and accelerated progression of AD. Subjects with two ε4 alleles account for 10%-14% of AD and exhibit an even more aggressive disease progression. ε4 allele leads to an increased brain Aβ amyloid deposition, increased CSF tau and p-tau, and faster cognitive decline. In addition, demented patients carrying one or two ε4 alleles of ApoE are more likely to have AD, resulting in significantly reduced rate of disease misdiagnosis in clinical studies (2% vs. 42% in non-ApoE4 patients).

In some embodiments, treatment or prevention are within the context of the present invention if there is a measurable difference between the performances of subjects treated using the compounds and methods provided herein as compared to members of a placebo group, historical control, or between subsequent tests given to the same subject.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens may depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg, about 250 mg, or about 500 mg and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I, Formula II, Formula III, Formula IV, Formula V, or Formula VI) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

In some embodiments, the dosage range for oral administration is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 800 mg, about 10 to about 700 mg, about 10 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 900 mg, about 50 mg to about 800 mg, about 50 to about 700 mg, about 50 mg to about 600 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 900 mg, about 100 mg to about 800 mg, about 100 to about 700 mg, about 100 mg to about 600 mg, about 100 mg to about 500 mg, about 100 mg to about 400 mg, about 100 mg to about 300 mg, about 100 mg to about 250 mg, about 100 mg to about 200 mg, about 100 mg to about 150 mg, about 150 mg to about 200 mg, about 150 mg to about 250 mg, about 150 to about 300 mg, about 150 mg to about 400 mg, about 150 mg to about 500 mg, about 200 mg to about 900 mg, about 200 mg to about 800 mg, about 200 to about 700 mg, about 200 mg to about 500 mg, about 200 mg to about 400 mg, about 200 mg to about 300 mg, about 200 mg to about 250 mg, about 300 mg to about 900 mg, about 300 mg to about 800 mg, about 300 to about 700 mg, about 300 to about 600 mg, about 300 mg to about 500 mg, about 300 mg to about 400 mg, about 400 mg to about 900 mg, about 400 mg to about 800 mg, about 400 mg to about 700 mg, about 400 to about 600 mg, about 400 mg to about 500 mg, about 500 mg to about 900 mg, about 500 mg to about 800 mg, about 500 to about 700 mg, about 500 to about 600 mg, about 100 mg to about 500 mg, about 100 mg to about 400 mg, about 100 mg to about 300 mg, or about 100 mg to about 250 mg. In an embodiment, the range is about 150 mg to about 400 mg.

In still further embodiments, the dose is 10 mg, 25 mg, 50 mg, 60 mg, 70 mg, 75 mg, 80 mg, 85 mg, 90 mg, 100 mg, 105 mg, 1 10 mg, 1 15 mg, 120 mg, 125 mg, 130 mg, 135 mg, 140 mg, 145 mg, 150 mg, 160 mg, 170 mg, 180 mg, 190 mg, 200 mg, 225 mg, 250 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

Administration of compounds and compositions provided herein can be carried out using known procedures, at dosages and for periods of time effective to achieve a desired purpose. Dosage regimens can be adjusted to provide the optimum therapeutic response. For example, several divided doses may be administered daily or the dose may be proportionally reduced as indicated by the exigencies of the therapeutic situation. In some embodiments, a compound or composition is administered at an effective dosage sufficient to prevent or treat an amyloid-β related disease, e.g., Alzheimer's disease, in a subject. Further, a compound or composition may be administered using any suitable route or means, such as without limitation via oral, parenteral, intravenous, intraperitoneal, intramuscular, sublingual, topical, or nasal administration, via inhalation, or via such other routes as are known in the art.

In some embodiments, the efficacy of a compound may be determined through use of a cognitive test known in the art, such as the ADAS-cog (Alzheimer's Disease Assessment Scale-cognitive subscale). ADAS was designed to measure the severity of the most important symptoms of Alzheimer's disease (AD). The ADAS-Cog helps evaluate cognition and differentiates between normal cognitive functioning and impaired cognitive functioning. It is especially useful for determining the extent of cognitive decline and can help evaluate which stage of Alzheimer's disease a person is in, based on his answers and score. The ADAS-Cog can be used in clinical trials in order to determine incremental improvements or declines in cognitive functioning. An increased ADAS-Cog score compared to placebo demonstrates improved cognitive functioning.

The compounds and compositions provided herein may be administered once, twice, three, or four times daily, using any suitable mode described above. Also, in certain embodiments, administration or treatment with the compounds according to any of the formulae described herein may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with the compounds according to any of the formulae described herein may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with the compounds according to any of the formulae described herein may be continued indefinitely. In still further embodiments, administration or treatment with the compounds according to any of the formulae described herein may be continued until the ADAS-Cog score improves by about 1.5-fold to about 4.5-fold. In some aspects, the improvement in score is about 1.5-fold, about 2.0-fold, about 3.5-fold, about 4.0-fold, about 4.5-fold, about 5.0-fold, about 7.5-fold, about 10.0-fold, about 15.0-fold. In particular aspects, the improvement is about 1.5-fold to about 10.0-fold.

It should be understood that compounds and/or compositions provided herein may be used alone or in combination with other therapies. Non-limiting examples of other amyloid-β related disease therapies include cognitive enhancers (e.g., acetylcholinesterase inhibitors, NMDA receptor antagonists), other amyloid-β binding compounds, and so on. Thus, compounds and/or compositions described herein may be administered alone or in combination with one or more additional therapy that may be available over-the-counter or by prescription. The latter can be administered before, after or simultaneously with the administration of the compounds and/or compositions described herein. U.S. Patent Application Publication No. 2005/0031651 (incorporated herein by reference) provides a long but non-exhaustive list of "therapeutic drugs" that can be useful, in combination, according to the invention. Non-limiting examples of therapeutic drugs to be used with the compounds or pharmaceutical compositions provided herein are therapeutic drugs useful in the prevention or treatment of Alzheimer's Disease (AD) or its symptoms, including but not limited to donepezil (Aricept™) memantine (Namenda™), rivastigmine (Exelon™), Galanthamine (Reminyl™ and R-flurbiprofen (Flurizan™). The compounds and compositions according to the invention could also be combined with vaccines and antibodies for the prevention or treatment of AD.

Kits

Compound and compositions provided herein may be packaged as part of a kit, optionally including a container (e.g. packaging, a box, a vial, etc). The kit may be commercially used according to the methods described herein and may include instructions for use in such methods. Additional kit components may include acids, bases, buffering agents, inorganic salts, solvents, antioxidants, preservatives, or metal chelators. The additional kit components may be present as pure compositions, or as aqueous or organic solutions that incorporate one or more additional kit components. Any or all of the kit components optionally further comprise buffers.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

General Methods for Preparation and Use of Compounds of the Invention.

General Method A. Preparation and use of 3-amino-1-propanesulfonic Acid (3APS) Sodium Salt.

3APS of natural abundance or isotope-enriched was dissolved in water, followed by addition of 1 molar equivalent of sodium hydroxide. The mixture was kept at room temperature (r.t.) for 10 min., concentrated to dryness, and further dried under vacuum. The solid residue was sodium salt of 3APS, which was used in the following synthesis without purification.

General Method B. De-Salting using Ion-Exchange Resin.

Crude product containing sodium chloride or sodium bromide (e.g., 2 mmol) was dissolved in water (e.g., 5 mL), followed by addition of Amberlite IR-120 (H-form) (2 mL). The mixture was stirred for 3 min. and filtered. The resin was washed with water (e.g., 2 mL×3). The filtrate and washings were combined, and treated with resin once more. An optional third treatment with resin was done if there was chloride or bromide ion remaining in the solution. The aqueous solution thus obtained was concentrated to dryness (rotary evaporator), and further dried to give salt-free product.

Example 1. Synthesis of 3-amino-3,3-dideuterium-1-propanesulfonic acid (1) and sodium 3-amino-3,3-dideuterium-1-propanesulfonate (1s)

3-Hydroxypropanenitrile (26.0 g, 366 mmol, 1.0 eq.) was dissolved in dry THF (50 mL). The solution was added dropwise to a stirring suspension of LiAlD$_4$ (10.0 g, 238 mmol, 0.65 eq.) in dry THF (200 mL). After heating at reflux overnight, the reaction mixture was hydrolyzed at r.t. by slow addition of water (4.8 mL), 15% NaOH solution (4.8 mL), and water (14.4 mL) subsequently. The mixture was stirred for 2 hours (h), and filtered under reduced pressure. The organic phase from the filtration was evaporated to dryness, giving a red oil material, which was used in the next step without purification.

The oil material (10.0 g, 128 mmol, 1.0 eq.) was dissolved in CHCl$_3$ (100 mL) and stirred at 0° C. To the stirred mixture was added dropwise SOCl$_2$ (18.2 g, 154 mmol, 1.2 eq.). The mixture was heated at reflux overnight, and then evaporated to dryness under reduced pressure. The residual material was purified by column chromatography on silica gel using 10-30% MeOH—CH$_2$Cl$_2$ as eluent to afford 3-chloro-1,1-dideuterium-1-propylamine hydrochloride (10.8 g, 64.4%) as a white solid.

The above obtained white solid material (10.0 g, 76.3 mmol, 1.0 eq.) was dissolved in water (50 mL), followed by addition of Na$_2$SO$_3$ (9.61 g, 76.3 mmol, 1.0 eq.). The mixture was heated at reflux overnight and evaporated to dryness under reduced pressure, followed by addition of concentrated HCl. The insoluble material (NaCl) was removed by filtration, and the filtrate was carefully evaporated to dryness. The resultant was purified by recrystallization using H$_2$O and EtOH. The solid was collected by filtration, and then dried to give the title compound (1) as a white solid (9.5 g, 88.3%). $^1$H NMR (500 MHz, D$_2$O): δ ppm 2.15 (t, J=7.5 Hz, 2H), 3.07 (t, J=7.5 Hz, 2H); $^{13}$C NMR (125 MHz, D$_2$O): δ ppm 22.21, 37.74 (m, CD$_2$), 47.87; m/z (ES$^-$) 140.0 (M−H).

To a solution of compound 1 in water (10 mL) was added NaOH (1.0 eq.), and the mixture was stirred for 10 min at r.t. The mixture was evaporated under reduced pressure to dryness, giving compound 1s, which was used for further reaction without purification.

Example 2. Synthesis of 3-((L-alanyl)amino)-3,3-dideuterium-1-propanesulfonic acid (2)

Compound 1s (0.30 g, 1.80 mmol, 1.0 eq.) and N-Boc-L-alanine (0.37 g, 2.0 mmol, 1.1 eq.) were mixed in dry DMF (10 mL) and cooled to 0° C., followed by addition of DCC (0.56 g, 2.7 mmol, 1.5 eq.) and HOBt (0.24 g, 1.80 mmol, 1.0 eq.) at 0° C. The mixture was stirred overnight at r.t., followed by addition of water (2 mL), and stirred for an additional hour. The insoluble material was removed by filtration, and the organic phase of the filtrate was evaporated to dryness. The residual material was dissolved in 20 mL water and washed with ethyl acetate (2×20 mL). The aqueous layer was evaporated to dryness. The residue was purified by column chromatography on silica gel using 10-30% MeOH—CH$_2$Cl$_2$ as eluent to afford sodium 3-((N-Boc-L-alanyl)amino)-3,3-dideuterium-1-propanesulfonic acid the (0.50 g, 81.3%) as a white solid. This white solid (0.50 g, 1.5 mmol, 1.0 eq.) was added to 1N HCl (10 mL); and the mixture was stirred at 50° C. for 2 h, and evaporated to dryness. The salt was removed by using ion-exchange resin (as described in General Method B above). The crude material was purified by recrystallization (MeOH and ethyl acetate). The solid product was collected by filtration, and dried under reduced pressure, giving title compound (2) (277 mg, 87.3%) as a white solid. $^1$H NMR (500 MHz, D$_2$O): δ ppm 1.49 (d, J=7.0 Hz, 3H), 1.92 (t, J=8.0 Hz, 2H), 2.90 (t, J=8.0 Hz, 2H), 3.97-4.07 (m, 1H), 8.34 (s, 1H); $^{13}$C NMR (125 MHz, D$_2$O): δ ppm 16.47, 23.71, 48.30, 49.10, 170.69; m/z (ES$^-$) 210.8 (M−H).

Example 3. Synthesis of 3-(L-serylamino)-3,3,-dideuterium-1-propanesulfonic acid (3)

Compound 1s (806 mg, 5.0 mmol, 1.0 eq.) and N-Boc-L-serine (1.03 g, 5.0 mmol, 1.0 eq) were mixed in DMF (5 mL), followed by addition of diphenylphosphoryl azide (DPPA) (1.51 g, 5.0 mmol, 1.0 eq) and Et$_3$N (0.77 mL). The mixture was stirred at r.t. overnight, and concentrated under reduced pressure. The residue was purified by flash column chromatography (MeOH/DCM, 1:4), giving sodium 3-((N-Boc-L-seryl)amino)-3,3,-dideuterium-1-propanesulfonic acid (800 mg, 58.0%) as a white solid. The solid material (250 mg, 0.71 mmol, 1.0 eq.) was added into 1N HCl aqueous solution (10 mL), and the mixture was stirred at r.t. for 1 h, concentrated under reduced pressure. The salt was removed by using ion-exchange resin (as described in General Method B above). The product was dried under vacuum, affording the title compound (3) (150 mg, 92.6%) as a white solid. $^1$H NMR (500 MHz, D$_2$O) δ ppm 1.84-1.94 (m, 2H), 2.78-2.94 (m, 2H), 3.83-3.98 (m, 2H), 4.08-4.14 (m, 1H); $^{13}$C NMR (125 MHz, D$_2$O) δ ppm 23.70, 37.80, 48.30, 54.57, 60.16, 167.59; m/z (ES$^+$) 228.9 (M+H).

Example 4. Synthesis of 3-((L-valyl)amino)-3,3-dideuterium-1-propanesulfonic acid (4)

Compound 1s (1.63 g, 10.0 mmol, 1.0 eq; prepared from compound 1 and sodium hydroxide) and N-Boc-L-valine (2.60 g, 12.0 mmol, 1.2 eq.) were dissolved in dry DMF (20 mL), followed by, at 0° C., addition of N,N'-dicyclohexylcarbodiimide (DCC, 2.47 g, 12.0 mmol, 1.2 eq.) and hydroxybenzotriazole (HOBt, 1.35 g, 10.0 mmol, 1.0 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel using 10-30% MeOH—CH$_2$Cl$_2$ as eluent, providing sodium 3-((N-Boc-L-valyl)amino)-3,3-dideuterium-1-propanesulfonic acid as a white solid (3.2 g, 88.3%).

The above obtained Boc-protected compound (3.2 g, 8.83 mmol, 1.0 eq.) was stirred in 1N HCl (30 mL) at 50° C. for 2 h. The mixture was evaporated to dryness and the crude material. The salt was removed using ion-exchange resin (General Method B) and the crude was purified by recrystallization using MeOH and ethyl acetate. The crystalline solid was collected by filtration, dried under reduced pressure, giving the title compound (4) (1.87 g, 88.1%) as a white solid. $^1$H NMR (500 MHz, D$_2$O): δ ppm 0.92-1.06 (m, 6H) 1.98 (t, J=7.5 Hz, 2H), 2.17-2.21 (m, 1H), 2.95 (t, J=8.0 Hz, 2H), 3.76 (d, J=6.5 Hz, 1H); $^{13}$C NMR (125 MHz, D$_2$O): δ ppm 17.01, 17.57, 23.73, 29.80, 48.40, 58.78, 169.18; m/z (ES$^-$) 239.1 (M−H).

Example 5. Synthesis of 3-((L-phenylalanyl)amino)-3,3-dideuterium-1-propanesulfonic acid (5)

Compound 1s (815 mg, 5.0 mmol, 1.0 eq.) and N-Boc-L-phenylalanine (1.59 g, 6.0 mmol, 1.2 eq.) were mixed in dry DMF (20 mL). The mixture was cooled to 0° C., followed by addition of DCC (1.24 g, 6.0 mmol, 1.2 eq.) and HOBt (675 mg, 5.0 mmol, 1.0 eq.) at 0° C. The reaction mixture was stirred at r.t. overnight, followed by addition of water (2 mL), and then stirred for 1 h. The solid material was removed by filtration, and the organic phase of the filtrate was evaporated to dryness. The residual material was dissolved in water (20 mL), and the aqueous solution was washed with ethyl acetate (2×20 mL). The aqueous phase was separated and evaporated to dryness. The residual material was purified by column chromatography on silica gel (eluent: methanol in $CH_2Cl_2$, from 10 to 30%), affording sodium 3-((N-Boc-L-phenylalanyl)amino)-3,3-dideuterium-1-propanesulfonic acid (1.80 g, 87.7%) as a white solid. This white solid (1.80 g, 4.39 mmol, 1.0 eq.) was treated with 1M HBr (20 mL) at 50° C. for 2 h, then the solvent was evaporated to dryness. The residual material was purified by recrystallization (EtOH and ethyl acetate). The solid was collected by filtration, and dried under reduced pressure, giving the title compound, 5, (1.07 g, 84.5%) as a white solid. $^1H$ NMR (500 MHz, $D_2O$): δ ppm 1.67-1.80 (m, 2H), 2.54-2.68 (m, 2H), 3.05-3.28 (m, 2H), 4.14 (t, J=6.5 Hz, 1H), 7.28 (d, J=9.0 Hz, 2H), 7.34-7.47 (m, 3H); $^{13}C$ NMR (125 MHz, $D_2O$): δ ppm 23.44, 36.87, 37.5 (m, $CD_2$), 48.18, 54.64, 128.04, 129.17, 129.27, 133.86, 168.81; m/z (ES$^-$) 287.0 (M–H).

Example 6. Synthesis of 3-((L-histidyl)amino)-3,3-dideuterium-1-propanesulfonic acid hydrochloride (6)

Compound 1s (0.93 g, 5.74 mmol, 1.0 eq.) and N-Boc-L-histidine (1.47 g, 5.74 mmol, 1.0 eq.) were mixed in DMF (10 mL), followed by addition of DPPA (1.74 g, 1.1 eq.) and $Et_3N$ (0.88 mL, 1.1 eq.). The mixture was stirred at r.t. overnight. After removal of solvent under reduced pressure, the residual material was purified by flash column chromatography (MeOH/DCM, 1:3), affording sodium 3-((N-Boc-L-histidyl)amino)-3,3-dideuterium-1-propanesulfonic acid (1.4 g, 60.9%) as a white solid. The solid was added into 1N HBr aqueous solution (10 mL). The mixture was stirred at r.t. for 1 h, concentrated under reduced pressure. The residual material was purified by recrystallization (EtOH and $H_2O$). The solid was collected by filtration, and dried under reduced pressure, giving the title compound (6) (1.25 g, 99.0%) as a white solid. $^1H$ NMR (500 MHz, $D_2O$) δ ppm 1.82 (d, J=6.8 Hz, 2H), 2.78 (t, J=7.0 Hz, 2H), 3.37 (s, 2H), 4.21 (d, J=6.0 Hz, 1H), 7.44 (s, 1H), 8.71 (s, 1H); $^{13}C$ NMR (125 MHz, $D_2O$) δ ppm 23.55, 25.99, 48.21, 52.30, 118.30, 125.91, 134.32, 167.69; m/z (ES$^+$) 278.9 (M+H).

Example 7. Synthesis of 3-($^{15}$N-amino)-1-propanesulfonic acid (7)

To a solution of 1,3-propanesultone (0.61 g, 5.0 mmol, 1.0 eq.) in MeOH (10 mL) in a sealed tube was added $^{15}$N-labeled ammonium sulfate (1.0 g, 7.5 mmol, 1.5 eq.) and NaOH (0.5 g, 12.5 mmol, 2.5 eq.). The mixture was stirred overnight at 70° C., followed by addition of $NaHCO_3$ (0.63 g, 7.5 mmol, 1.5 eq.) and di-(tert-butyl)dicarbonate (1.64 g, 7.5 mmol, 1.5 eq.). After heating at reflux for 3 h, the reaction mixture was evaporated to dryness. The residual material was treated with MeOH and the insoluble material was removed by filtration. The filtrate was evaporated to dryness, and the residual material was purified by flash column chromatography on silica gel (eluent: 30% MeOH-DCM) to afford a waxy solid. This material was treated with 1N HBr (20 mL) and the mixture was stirred at 50° C. for 2 h. The mixture was evaporated to dryness and the residual material was purified by recrystallization (EtOH and $H_2O$). The solid was collected by filtration, and dried under reduced pressure, giving 3-($^{15}$N-amino)-1-propanesulfonic acid (7) (398 mg, 56.8%) as a white solid. $^1H$ NMR (500 MHz, $D_2O$): δ ppm 2.06-2.16 (m, 2H), 3.01 (t, J=7.5 Hz, 2H), 3.15 (t, J=7.5 Hz, 2H); $^{13}C$ NMR (125 MHz, $D_2O$): δ ppm 22.23, 38.17 (d, J=5.0 Hz), 47.82; m/z (ES$^+$) 140.8 (M+H).

Example 8. Synthesis of 3-(L-valyl-($^{15}$N-amino))-1-propanesulfonic acid (10)

To a solution of 1,3-propanesultone (1.22 g, 10.0 mmol, 1.0 eq.) in 20 mL MeOH/$H_2O$ (1:1) in a sealed tube was added $^{15}$N-labeled ammonium sulfate (2.0 g, 15.0 mmol, 1.5 eq.) and NaOH (1.0 g, 25 mmol, 2.5 eq.). The mixture was stirred overnight at 70° C., followed by addition of triethylamine (1.51 g, 15.0 mmol, 1.5 eq.) and di-tert-butyl dicarbonate (3.27 g, 15.0 mmol, 1.5 eq.). After heating at reflux for 3 h, the reaction mixture was evaporated to dryness. The residual material was treated with MeOH and the insoluble material was removed by filtration. The filtrate was evaporated to dryness and the residual material was purified by flash column chromatography on silica gel (eluent: 30% MeOH-DCM) to afford a waxy solid. This material was treated with 1N HCl (30 mL) and the mixture was stirred at 50° C. for 2 h. The mixture was evaporated to dryness and the residual material, 3-($^{15}$N-amino)-1-propanesulfonic acid (7), was used in the next step without further purification.

To a solution of compound 7 in 10 mL $H_2O$ was added NaOH (0.4 g, 10.0 mmol, 1.0 eq.), and the mixture was stirred for 10 min at r.t. The mixture was evaporated to dryness to give sodium salt of 7, which was used in the next step without further purification.

The sodium salt of 7 (obtained above) and N-Boc-L-valine (3.26 g, 15.0 mmol, 1.5 eq.) were mixed in dry DMF (30 mL), cooled to 0° C., followed by addition of DCC (3.09 g, 15.0 mmol, 1.5 eq.) and HOBt (1.35 g, 10.0 mmol, 1.0 eq.). The reaction mixture was stirred overnight at r.t., followed by addition of water (2 mL), and stirred for 1 h. The insoluble material was removed by filtration, and the organic layer of the filtrate was evaporated to dryness. The residual material was dissolved in 20 mL water and the aqueous solution was washed with ethyl acetate (2×20 mL). The aqueous phase was evaporated to dryness; and the residual material was purified by column chromatography on silica gel (eluent:10 to 30% MeOH/$CH_2Cl_2$), giving a waxy solid, which was treated with 1N HCl (30 mL) and stirred at 50° C. for 2 h. The mixture was evaporated to dryness and the salt was removed by using ion-exchange resin (General Method B). The residual material was purified by recrystallization (EtOH and $H_2O$). The solid was collected by filtration and dried under reduced pressure, giving the title compound (10) (1.23 g, 51.4%) as a white solid. $^1H$ NMR (500 MHz, $D_2O$): δ ppm 0.99-1.08 (m, 6H), 1.91-2.03 (m, 2H), 2.12-2.25 (m, 1H), 2.93 (t, J=9.0 Hz, 2H), 3.32-3.45 (m, 2H), 3.74 (d, J=6.0 Hz, 1H); $^{13}C$ NMR (125 MHz, $D_2O$): δ ppm 16.97, 17.54, 23.88, 29.77, 38.03 (d, J=8.8 Hz), 48.39, 58.74 (d, J=8.8 Hz), 169.13 (d, J=17.5 Hz); m/z (ES$^-$) 237.9 (M–H).

Example 9. Synthesis of 3-(($^{18}$O-L-alanyl)amino)-1-propanesulfonic acid (13)

L-Alanine (0.91 g, 10.2 mmol, 1 eq.) was added to a solution of 4M HCl in dioxane (5.2 mL, 20.8 mmol, 2 eq.), followed by addition of H$_2$$^{18}$O (1.8 mL; $^{18}$O-enrichment, 98%). The mixture was stirred in a sealed tube at 100° C. for 24 h, cooled to r.t., and evaporated to dryness. The residual material was taken into a solution of 4M HCl in Dioxane (2.6 mL, 10.2 mmol, 1 eq.), followed by addition of H$_2$$^{18}$O (1.6 mL, $^{18}$O-enrichment, 98%). The mixture was stirred in a sealed tube at 100° C. for 24 h, cooled to r.t., and evaporated to dryness under reduced pressure, affording L-alanine-$^{18}$O$_2$.HCl (1.32 g, 100%; $^{18}$O-enrichment, 92%) as a white solid. To the solution of L-alanine-$^{18}$O$_2$.HCl (1.32 g, 10.2 mmol, 1 eq.) 1 in MeOH (50 mL) was added N,N-diisopropylethylamine (DIPEA) (4.07 mL, 22.5 mmol, 2.2 eq.), followed by addition of Boc$_2$O (2.55 g, 11.2 mmol, 1.1 eq.). The mixture was stirred at 50° C. for 1 h (the mixture became clear at this point), cooled to r.t., and concentrated to dryness under reduced pressure, affording N-Boc-L-alanine-$^{18}$O$_2$ DIPEA salt as a white solid, which was used in the next step without further purification. The DIPEA salt (1 eq., obtained from the above step) was added to a solution of p-nitrophenol (1.59 g, 11.22 mmol, 1.1 eq.) in DMF (40 mL), followed by addition of DCC (3.21 g, 15.3 mmol, 1.5 eq.). The mixture was stirred at r.t. overnight. The reaction mixture was filtered, and the filtrate was concentrated under reduced pressure. The residue was purified by flash column chromatography (ethyl acetate/pet-ether, 1:10) to afford the corresponding p-nitrophenyl ester as a white solid. The solid thus obtained was dissolved in DMF (30 mL), followed by addition of sodium 3-amino-1-propanesulfonate (1.72 g, 10.2 mmol, 1.0 eq.). The mixture was stirred at 35° C. overnight, and then concentrated under reduced pressure. The residue was purified by flash column chromatography (eluent: MeOH/DCM, 1:8), affording sodium 3-((N-Boc-L-$^{18}$O-alanyl)amino)-1-propanesulfonic acid (1.5 g, 4.49 mmol; overall yield for the above steps, 44%) as a white solid. Sodium 3-((N-Boc-L-$^{18}$O-alanyl) amino)-1-propanesulfonic acid (1.5 g, 4.49 mmol) was dissolved in 1N HCl aqueous solution (20 mL). The mixture was stirred at r.t. for 1 h, and evaporated to dryness. The salt was removed by using ion-exchange resin (General Method B). The product was dried under vacuum, affording the title compound (13) (0.78 g, 82.0%) as a white solid. $^{18}$O-enrichment, 92%; $^1$H NMR (D$_2$O, 500 MHz) δ ppm 1.46-1.51 (m, 2H), 1.88-1.97 (m, 2 H), 2.86-2.92 (m, 2H), 3.30-3.37 (m, 2H), 4.20 (q, 1H, J=5 Hz); $^{13}$C NMR (D$_2$O, 125 MHz) δ ppm 16.45, 23.88, 38.05, 48.33, 49.08, 170.62; m/z (ES$^-$) 211.0 (M–H).

Example 10. Synthesis of 3-(($^{18}$O-L-valyl)amino)-1-propanesulfonic acid (15)

To a solution of L-Valine (1.2 g, 10.2 mmol) in $^{18}$O-water (1.5 g, 75.0 mmol, 98 atom % $^{18}$O) was added slowly 4N HCl in 1,4-dioxane (5.1 mL, 20.4 mmol). The mixture was sealed with stopper, heated at 100° C. for 24 h, and then cooled to r.t., and and evaporated (up to 60° C. bath temperature) to dryness. The above process was repeated once, giving $^{18}$O-L-Valine hydrochloride as a yellow solid (1.57 g, 100%, 91.4 atom % $^{18}$O), which was used for the next step directly.

To a solution of $^{18}$O-L-Valine hydrochloride (1.57 g, 10.2 mmol, 1.0 eq.) in MeOH (25 mL) was added DIPEA (2.6 g, 20.4 mmol, 2.0 eq.), followed by addition of Boc$_2$O (2.2 g, 10.2 mmol, 1.0 eq.). The mixture was heated at 55° C. for 30 min, cooled to r.t., and concentrated in vacuo to dryness, giving N-Boc-L-$^{18}$O-valine (used in the next step without purification). This material was taken into CH$_2$Cl$_2$ (30 mL), and the solution was cooled to 0° C., followed by addition of 4-nitrophenol (1.5 g, 10.7 mmol, 1.05 eq.) and DCC (2.3 g, 11.2 mmol, 1.1 eq.) at 0° C. The mixture was stirred for 2 h at r.t. TLC analysis (DCM: MeOH=10:1) showed no starting material remaining. The insoluble material was removed by filtration, and washed with DCM (30 mL). The combined filtrate was concentrated, and purified by silica gel chromatography (EtOAc:hexane, 4:1), giving a yellow liquid (2.8 g, 80.2%). This liquid (2.2 g, 6.4 mmol, 1.0 eq.) and sodium 3-amino-1-propanesulfonate (1.0 g, 6.4 mmol, 1.0 eq.) were mixed in DMF (22 mL). The mixture was stirred at 35° C. for 24 h. The solvent was removed under reduced pressure, and the residue was purified by silica gel chromatography (DCM:MeOH, 4:1), giving sodium 3-((N-Boc-($^{18}$O-L-valyl))amino)-1-propanesulfonic acid as a white solid (1.5 g, 65.0%).

The solution of the above obtained solid (1.5 g, 4.1 mmol) in 1N HCl (20 mL) was stirred at 60° C. for 1 h. The solvent was removed under reduced pressure. The salt was removed by using ion-exchange resin (General Method B). The product was dried under vacuum, affording the title compound, 15 (686 mg, 70.0%) as a white solid. $^{18}$O-Enrichment, 94% (by ES-MS); $^1$H NMR (500 MHz, D$_2$O) δ ppm 0.98-1.10 (m, 6H), 1.97 (s, 2H), 2.20 (d, J=4.8 Hz, 1H), 2.93 (s, 2H), 3.38 (d, J=4.5 Hz, 2H), 3.75 (s, 1H); $^{13}$C NMR (126 MHz, D$_2$O) δ ppm 17.05, 17.61, 23.94, 29.82, 38.13, 48.47, 58.78, 169.15; m/z (ES$^-$) 238.9 (M–H).

Example 11. Synthesis of 3($^{18}$O-L-phenylalanyl) amino)-1-propanesulfonic acid (16)

To a mixture of L-phenylalanine (1.0 g, 6.05 mmol, 1.0 eq.) and $^{18}$O-water (1.3 mL, 98 atom % $^{18}$O) was added a saturated hydrochloride (HCl) solution in 1,4-dioxane (3.0 mL, 12.0 mmol, 2.0 eq.). The mixture was stirred at 100° C. for 24 h, then cooled to r.t., and evaporated to dryness under reduced pressure. To the residual material was added $^{18}$O-water (1.5 mL, 98 atom % $^{18}$O), followed by addition of HCl solution in 1,4-dioxane (1.6 mL). The mixture was stirred at 100° C. for 24 h, then cooled to r.t., and evaporated to dryness under reduced pressure, giving $^{18}$O-L-phenylalanine as a white solid (1.0 g, 100%; 96% of $^{18}$O-enrichment).

To $^{18}$O-L-phenylalanine (1.0 g, 6.1 mmol, 1.0 eq.) in methanol (20 mL) was added (Boc)$_2$O (1.45 g, 6.65 mmol, 1.1 eq.) and triethylamine (1.8 g, 18.0 mmol, 3.0 eq.). The mixture was stirred at 30° C. for 2 h, then evaporated to dryness under reduced pressure. The residue was dissolved in dichloromethane (10 mL), followed by addition of dicycylohexylcarbodiimide (1.24 g, 6.1 mmol, 1.0 eq.) and N-hydroxysuccinimide (0.60 g, 6.2 mmol, 1.05 eq.). The mixture was stirred at r.t. overnight. The insoluble material was removed by filtration, and the filtrate was evaporated under reduced pressure. The residual material was purified by flash column chromatography on silica gel (eluent: CH$_2$Cl$_2$/methanol, 10:1), giving a white solid (1.4 g). This white solid was dissolved in DMF (20 mL), followed by addition of sodium 3-aminopropane-1-sulfonate (610 mg, 3.84 mmol). The mixture was stirred at r.t. for 2 h, and solvent was removed in vacuo. The residual material was purified by flash column chromatography on silica gel (eluent: CH$_2$Cl$_2$/methanol, from10:1 to 5:1), giving sodium 3-((N-Boc-($^{18}$O-L-phenylalanyl))amino)-1-propanesulfonic acid as a white solid (1.3 g, 82.0%). The obtained compound was dissolved in 1N HCl (20 mL). The mixture was stirred for 4 h, and then concentrated in vacuo. The salt was removed by using ion-exchange resin (General Method B). To the residual material was added ethanol (20 mL), and the mixture was stirred at r.t. for 5 min. The solid was collected by filtration, washed with ethanol (5 mL), and dried under reduced pressure, affording the title compound (400 mg, 40.0%) as a white solid. $^{18}$O-enrichment, 87%; $^1$H NMR (500 MHz, D$_2$O) δ ppm 1.68-1.69 (m,2H), 3.02-3.10 (m, 2H), 2.53-2.56 (m, 2H), 3.14-3.24 (m, 2H), 4.06 (t, J=8.0 Hz, 1H), 7.21 (d, J=7.0 Hz, 2H), 7.32-7.37 (m, 3H), 8.09 (s, 1H); $^{13}$C NMR (125 MHz, D$_2$O) δ ppm 23.6, 36.8, 38.0, 48.1, 54.6, 128.0, 129.1, 129.2, 133.8, 168.7; m/z (ES$^+$) 288.9 (M+H), 310.9 (M+Na).

Example 12. Synthesis of 3-(($^{18}$O-L-histidyl) amino)-1-propanesulfonic acid hydrobromide (17)

L-Histidine (1.55 g, 10 mmol, 1.0 eq.) was added to a solution of 4M HCl in Dioxane (7.5 mL, 30 mmol, 3.0 eq.), followed by addition of H$_2$$^{18}$O (2.0 g, 98% $^{18}$O-enrichment). The mixture was stirred in a sealed tube at 100° C. for 24 h. The reaction mixture was cooled to r.t., and dried under vacuum. To the residue was added 4M HCl in Dioxane (2.5 mL, 10 mmol, 1.0 eq.), followed by addition of H$_2$$^{18}$O (2.0 g, $^{18}$O-enrichment, 98%). The mixture was stirred in a sealed tube at 100° C. for 24 h. The reaction mixture was cooled to r.t., evaporated to dryness, and further dried under vacuum, to afford L-His-$^{18}$O$_2$.2HCl (2.32 g, 100%, with 93.8% of $^{18}$O-enrichment) as an off-white solid. The $^{18}$O-enriched L-histidine dihydrochloride (2.32 g, 10 mmol, 1.0 eq.) was dissolved in MeOH (50 mL), followed by addition of Et$_3$N (4.55 g, 45 mmol, 4.5 eq.) and Boc$_2$O (5.45 g, 25 mmol, 2.5 eq.) subsequently. The mixture was stirred at 50° C. for 1 h (the mixture became clear at this point) and then was cooled to r.t., and concentrated under reduced pressure, to afford the corresponding TEA salt as a light-yellow solid. This light-yellow material (1.0 eq.) was added to a solution of p-nitrophenol (1.39 g, 10 mmol, 1.0 eq.) in DCM (40 mL), followed by addition of DCC (2.27 g, 11 mmol, 1.1 eq.). The mixture was stirred at r.t. overnight. The insoluble material was removed by filtration, and the filtrate was concentrated under reduced pressure. The residual material was purified by flash column chromatography (eluent: DCM/EA/PE, 2:1:7) to afford the corresponding 4-nitrophenyl ester (3.0 g, 63.0%) as a white solid. The ester (3.0 g, 6.27 mmol, 1.0 eq.) was dissolved in DMF (30 mL), followed by addition of sodium 3-aminopropane-1-sulfonate (1.0 g, 6.27 mmol, 1.0 eq.). The mixture was stirred at r.t. overnight. The reaction mixture was concentrated under reduced pressure, and the residual material was purified by flash column chromatography (eluent: MeOH/DCM, 1:8) to afford sodium 3-((N,1-bisBoc-($^{18}$O-L-histidyl))amino)-1-propanesulfonic acid (2.27 g, 72.3%) as a white solid. The white solid (2.27 g, 4.7 mmol) was taken into 1N HBr aqueous solution (20 mL). The mixture was stirred at r.t. for 1 h, concentrated under reduced pressure, and dried under vacuum. The residual material was purified by recrystallization (EtOH and H$_2$O). The solid was collected by filtration, and dried under reduced pressure, affording the title compound (17) (1.5 g, 92.0%) as a white solid. $^{18}$O-enrichment, 93.7%; $^1$H NMR (D$_2$O, 500 MHz) δ ppm 1.77-1.94 (m, 2H), 2.72-2.88 (m, 2H), 3.22-3.32 (m, 1H), 3.32-3.46 (m, 3H), 4.18-4.28 (m, 1H), 7.47 (s, 1H), 8.74 (s, 1H); $^{13}$C NMR (D$_2$O, 125 MHz) δ ppm 23.75, 25.98, 38.17, 48.26, 52.33, 118.30, 125.95, 134.34, 167.68; m/z (ES$^+$) 279.0 (M+H).

Example 13. Synthesis of 3-((1-$^{13}$C-L-valyl) amino)-1-propanesulfonic acid (25)

Sodium 3-amino-1-propanesulfonic acid (1.10 g, 6.8 mmol, 1.5 eq.) and N-Boc-L-valine-1-$^{13}$C (1.0 g, 4.61 mmol, 1.0 eq.) were dissolved in dry DMF (10 mL), followed by, at 0° C., addition of N,N'-dicyclohexylcarbodiimide (DCC, 1.4 g, 6.8 mmol, 1.5 eq.) and hydroxybenzotriazole (HOBt, 0.62 g, 4.61 mmol, 1.0 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel (eluent, MeOH—CH$_2$Cl$_2$, 10-30%), providing sodium 3-((N-Boc-1-$^{13}$C-L-valyl)amino)-1-propanesulfonic acid as a white solid (1.2 g, 72.0%).

The above obtained Boc-protected compound (1.2 g, 3.3 mmol, 1.0 eq.) was stirred in 1N HCl aqueous solution (30 mL) at 50° C. for 2 h. The mixture was evaporated to dryness. The salt was removed using ion-exchange resin (General Method B). The residual material was purified by recrystallization (EtOH and H$_2$O). The solid was collected by filtration and dried under reduced pressure, giving the title compound (25) (0.65 g, 75.4%) as a white solid. $^1$H NMR (500 MHz, D2O): δ ppm 0.97-1.05 (m, 6H), 1.90-2.00 (m, 2H), 2.21-2.23 (m, 1H), 2.91 (t, J=7.5 Hz, 2H), 3.29-3.43 (m, 2H), 3.69-3.75(m, 1H), 8.49 (s, 1H); $^{13}$C NMR (125 MHz, D2O): δ ppm 16.97, 17.54, 23.87, 29.77, 38.04, 48.39, 58.50, 58.92, 169.14, 169.23; m/z (ES$^-$) 238.0 (M–H).

Example 14. Synthesis of 3-(($^{18}$O-L-valyl)amino)-3, 3-dideuterium-1-propanesulfonic acid (29)

Compound 1s (250 mg, 1.53 mmol, 1.0 eq.) and N-Boc-L-(1,1-di-$^{18}$O)-valine 4-notrophenyl ester (624 mg, 1.84 mmol, 1.2 eq.) were mixed in dry DMF (20 mL). The mixture was stirred overnight at r.t., followed by evaporation under reduced pressure to dryness. The residual material was purified by column chromatography on silica gel (eluent: MeOH in CH2Cl$_2$, 10 to 30%), affording sodium 3-((N-Boc-$^{18}$O-L-valyl)amino)-3,3-dideuterium-1-propanesulfonic acid (400 mg, 71.7%) as a white solid. This solid material was mixed with 1N HCl (30 mL); and the mixture was stirred at 50° C. for 2 h. The mixture was evaporated to dryness. The salt was removed by using ion-exchange resin (General Method B). The residual material was purified by recrystallization (EtOH and H$_2$O). The solid was collected by filtration and dried under reduced pressure, giving the title compound 29 (283 mg, 89.8%) as a white solid. $^1$H NMR (500 MHz, D$_2$O): δ ppm 1.00-1.08 (m, 6H), 1.97 (t, J=7.5 Hz, 2H), 2.16-2.26 (m, 1H), 2.94 (t, J=8.0 Hz, 2H), 3.75 (d, J=6.0 Hz, 1H), 8.48 (s, 1H); $^{13}$C NMR (125 MHz, D$_2$O): δ ppm 17.03, 17.59, 23.75, 29.81, 37.59 (m, CD$_2$), 48.42, 58.79, 169.16; m/z (ES$^-$) 240.9 (M–H).

Example 15. Synthesis of 3-((L-cysteyl)amino-)-3, 3-dideuterium-1-propanesulfonic acid (33)

Compound 1s (0.7 g, 4.3 mmol, 1.0 eq.) and N-Boc-L-cysteine (1.4 g, 4.3 mmol, 1.0 eq.) were dissolved in dry DMF (15 mL), followed by, at 0° C., addition of DCC (1.4 g, 6.5 mmol, 1.5 eq.) and HOBt (0.6 g, 4.6 mmol, 1.1 eq.). The mixture was stirred overnight at r.t., followed by addition of water (2 mL), and stirred for one more hour. The insoluble material was removed by filtration. The organic phase of the filtrate was evaporated to dryness. The residual material was dissolved in water (20 mL) and washed with ethyl acetate (2×20 mL). The aqueous phase was evaporated to dryness and the residue was purified by column chromatography on silica gel (eluent: MeOH—CH$_2$Cl$_2$, 10-30%), providing sodium N-Boc-3-((L-cysteyl)amino-)-3,3-dideuterium-1-propanesulfonic acid as a white solid (1.2 g, 59.8%). The above obtained Boc-protected compound (1.2 g, 2.57 mmol, 1.0 eq.) was stirred in 1N HCl (30 mL) at 50° C. for 2 h. The mixture was evaporated to dryness. The salt was removed by using ion-exchange resin (General Method B). The residual material was purified by recrystallization (EtOH and H$_2$O). The crystalline solid was collected by filtration and dried under reduced pressure, giving the title compound (33) (0.57 g, 83.3%) as a white solid. $^1$H NMR (500 MHz, D$_2$O): δ ppm 1.97 (t, J=7.5 Hz, 2H), 2.95 (t, J=6.0 Hz, 2H), 3.01-3.13 (m, 2H), 4.16 (t, J=6.0 Hz, 1H); $^{13}$C NMR (125 MHz, D$_2$O): δ ppm 23.70, 24.73, 48.34, 54.55, 167.83; m/z (ES$^+$) 244.9 (M+H).

Example 16. General Example for the Synthesis of Isotope-Enriched 3-((N-substituted)amino)-1-propanesulfonic acid and its Salt With experimental procedures described in Examples 1 to 15, with or without reasonable modification using general synthetic skills in the art, other compounds represented by Formulae I to VI can be synthesized. Examples of such compounds include, but are not limited to, 3-(acylamino)-3,3-dideuterium-1-propanesulfonic acid and 3-(acyl($^{15}$N-amino))-1-propanesulfonic acid, where the acyl group is selected from arginyl, aspartyl, asparigyl, cystyl, glutamyl, glutaminyl, glycyl, isoleucyl, leucyl, lysyl, methionyl, prolyl, selenocystyl, threonyl, tryptophanyl, tyrosyl, and 4-hydroxyisoleucyl. Similarly, 3-((1-$^{13}$C-acyl)amino)-1-propqnesulfonic acid, 3-((1-$^{18}$O-acyl)amino)-1-propanesulfonic acid, and 3-((1-$^{17}$O-acyl)amino)-1-propanesulfonic acid according to Formulae I and VI can be prepared with the same set of acyl groups. The acyl groups may also include other natural amino acids and/or carboxylic acids useful in pharmaceutical preparations. The compounds can also be prepared in their salt and ester forms using general synthetic skills.

Example 17. Evaluation of Compound Stability in Simulated Gastric Fluid (SGF)

Compounds were evaluated for stability in simulated gastric fluid (SGF). A solution of a compound in SGF (400 μg/mL) was incubated at 37° C. for 4 h. An aliquot of the sample was withdrawn, at time 0 and time 4 h, for concentration analysis on a LC-MS/MS instrument. The initial concentration (at time 0) of a compound was considered as 1, and the remaining concentration of the compound at 4-h time point was calculated and expressed as the percentage of the initial concentration. Exemplary results for compounds 1, 4, 5, 15, 16, and 17 are given in Table 5.

TABLE 5

Compound stability in SGF.

| Compound | Remaining (%) at 4 h |
|---|---|
| 1 | (100) |
| 4 | 107 |
| 5 | 99 |
| 15 | 104 |
| 16 | 96 |
| 17 | 101 |

Example 18. Evaluation of Compound Stability in Whole Mouse Blood

Compounds were also evaluated for stability in whole mouse blood. A sample of test compound in fresh mouse blood (at a concentration of 1.44 μM) was incubated at 37° C. for 4 h. An aliquot of the sample was withdrawn, at time 5 min. and time 4 h, for concentration analysis on a LC-MS/MS instrument after converting the blood sample to an analytical sample employing standard sample preparation procedures. The detailed recovery of the compound was not fully evaluated and optimized. The sample was analyzed for the parent compound and the therapeutic compound. Table 6 shows exemplary results for compounds 1, 2, 4, 5, 15, 16, 17 and 29 in which the test compound and compound 1 were analyzed at 5 min. and/or 4 h.

TABLE 6

Compound stability in mouse blood (initial concentration at 1.44 μM).

| | | Compound 1 conc. (μM) | |
|---|---|---|---|
| Compound | Compound conc. (μM) at 4 h | 5 min. | 4 h |
| 1 | 0.98 | 1.40 | 0.98 |
| 2 | 0.18 | N.D. | N.D. |
| 4 | 0.74 | 0.03 | 0.29 |
| 5 | 0.03 | 0.23 | 0.60 |
| 15 | 0.78 | 0.01 | 0.20 |
| 16 | 0.74 | 0.13 | 0.39 |
| 17 | 1.20 | 0.02 | 0.13 |
| 29 | 0.80 | 0.02 | 0.20 |

N.D.: Not Detected

Example 19. General Method for Pharmacokinetic Study of Compounds of the Invention A compound according to the invention is dissolved in water at a concentration determined by the desired dose and dosing volume for the specific animal to which the compound is to be administered. A calculated volume of dosing solution is administered to the animal (PO, SQ, IP, or IV). A blood sample is collected following administration of the compound at specific time points (such as 10 min., 30 min., 1 h, 2 h, 4 h, 8 h, and 12 h). The blood sample is converted to a plasma sample using standard techniques. A brain sample can also be collected after complete perfusion. The plasma and/or brain samples are analyzed to determine the concentration of relevant compounds (including e.g., administered compounds, therapeutic compounds (e.g., drugs) and metabolites).

Example 20. Pharmacokinetic Studies of Compounds of the Invention in an ICR Mouse Forty-two male ICR mice, body-weight of 19 to 21 g, are randomized into 7 groups. The animals are administered with an aqueous solution of a test compound by oral gavage. Blood samples are collected into tubes pre-loaded with heparin anticoagulating agent, at time 0.167, 0.5, 1, 2, 4, 8, and 12 h after administration. Blood samples are centrifuged, and plasma samples are isolated for analysis of the test compound (including compounds administered, metabolites, and/or prodrugs). A 400 μL blood sample is collected from each animal, and then the animal is put to sleep with barbiturate anesthesia; perfusion is performed (through the main vein of the heart) with saline at a rate of 5 mL/min., for 6 min. The brain is collected and kept at −40° C. until the sample is analyzed. The protein in the plasma is precipitated and the analytical sample is analyzed on an AB4000-Q-Trap UPLC-MS/MS instrument.

Figure 2:
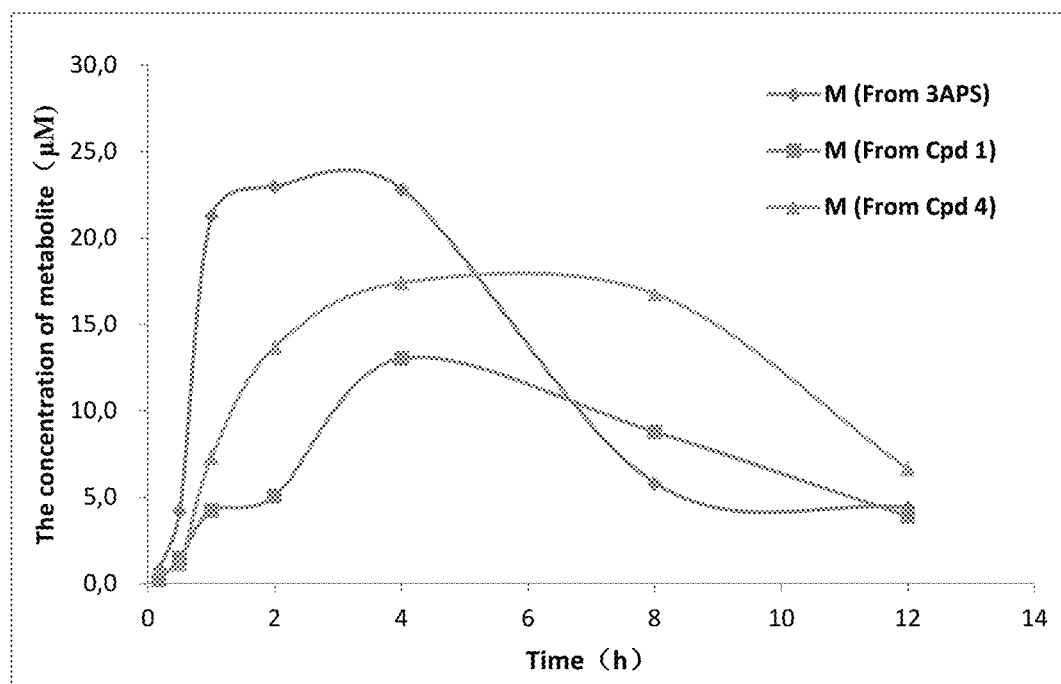
FIG. 2 shows the plasma concentration of the metabolite (M, 2-carboxy-1-ethanesulfonic acid) following an oral administration of non-isotope enriched 3APS (3APS of natural abundance), compound 1, and compound 4, respectively. Curves labeled with -♦-, -■-, and -▲- represent 3APS (of natural abundance), compound 1, and compound 4, respectively. All compounds were administered at a molar-equivalent dose (0.72 mmol/kg).

The results of an exemplary pharmacokinetic study are presented in FIGS. 1 and 2. FIG. 1 shows plasma compound concentration-time curves following an oral administration of 3APS (of natural abundance, i.e., not isotope-enriched), compound 1 and compound 4. In the figure, curves labeled with -♦-, -■-, and -▲- represent plasma drug concentration following administration of 3APS (of natural abundance), compounds 1 and 4, respectively; and the curve labeled with -x- represents plasma prodrug concentration following administration of 4. The results indicate that at the mole-equivalent oral dose, the isotope-enriched compounds 1 and 4 improved plasma drug exposure significantly, with close to 2-fold increase of Cmax for the drug concentration following the administration of 4. Furthermore, 4 (a prodrug of 1) was converted easily to 1 in the subject (FIG. 1). In addition, the isotope-enriched compounds (1 and 4) delayed drug metabolism.

FIG. 2 shows the plasma concentration of the metabolite (M, 2-carboxy-1-ethanesulfonic acid) following an oral administration of 3APS (of natural abundance), compound 1, and compound 4, with the curves labeled with -♦-, -■-, and -▲- representing 3APS (of natural abundance), 1, and 4, respectively. At the 2-h time point, for example, plasma drug concentrations from the compounds 1 and 4 were higher than that from 3APS (of natural abundance), while the concentration of metabolite in plasma was much lower following administration of isotope-enriched compounds compared to administration of 3APS (of natural abundance).

Example 21. Pharmacokinetic Studies for 3APS (of Natural Abundance), Compound 1 and Compound 4 in Sprague-Dawley (SD) Rats Pharmacokinetic studies were performed in Sprague-Dawley (SD) rats. The experiments were done using the same protocol described in Example 21, with 18 animals divided into three groups (6 in each group: one group for 3APS (of natural abundance), one group for compound 1, and the other group for compound 4). The primary PK parameters and results of the study are summarized in Table 7.

TABLE 7

PK parameters for 3APS (of natural abundance), compound 1, and compound 4 in SD rats.

| Parameter | Unit | 3APS | Compound 1 (following administration of) | |
|---|---|---|---|---|
| | | | 1 | 4 |
| AUC(0-t) | μg · h/L | 47212 | 53916 | 66900 |
| $t_{1/2}$ | h | 3.7 | 3.7 | 2.4 |
| $T_{max}$ | h | 0.5 | 0.5 | 0.4 |
| $C_{max}$ | μg/L | 18707 | 23017 | 32216 |

Example 22. Pharmacokinetic Studies for Compounds in C57Bl6 Mice

Pharmacokinetic studies were performed in C57B16 mice. The experiments were done using the same protocol described in Example 20. For each compound, 42 animals were used (6 animals per time point, and 7 time points distributed at 10 min, 0.5, 1, 2, 4, 8 and 12 h). The primary PK parameters and results of the study are summarized in Table 8.

TABLE 8

PK parameters from C57Bl6 mouse experiments.

| | Drug | | | Metabolite | | | Prodrug | | |
|---|---|---|---|---|---|---|---|---|---|
| Compd | $AUC_t$ | $C_{max}$ | $T_{1/2}$ | $AUC_t$ | $C_{max}$ | $T_{1/2}$ | $AUC_t$ | $C_{max}$ | $T_{1/2}$ |
| 1 | 27915 | 6685 | 2.1 | 22615 | 2795 | 12.8 | n/a | n/a | n/a |
| 2 | 21972 | 10513 | 1.8 | 12573 | 1751 | 11.8 | 348 | 472 | 0.6 |
| 3 | 17258 | 7020 | 1.9 | 14302 | 2018 | 4.2 | 44735 | 22300 | 1.9 |
| 4 | 38926 | 15622 | 2.0 | 21009 | 2828 | 5.7 | 38009 | 39483 | 1.5 |
| 5 | 20031 | 6426 | 2.4 | 2254 | 347 | 8.4 | 782 | 1092 | 0.4 |
| 6 | 25379 | 10013 | 2.1 | 24390 | 3678 | 3.5 | 16623 | 9920 | 1.4 |
| 13 | 26574 | 9930 | 1.9 | 21342 | 3576 | 4.5 | 1832 | 672 | 0.5 |
| 16 | 9391 | 2590 | 1.0 | 2155 | 273 | 5.1 | 11891 | 3843 | 1.5 |
| 17 | 31443 | 13888 | 2.4 | 23267 | 3738 | 3.6 | 14236 | 18983 | 1.1 | n/a: Not applicable

Example 23. Efficacy of Compounds of the Invention in an Animal Model of Alzheimer's Disease 100 APP/PS1 transgenic mice (7 months old, both male and female) are randomized into 5 groups (20 in each group): model control, positive control, and test groups of low-, medium-, and high-doses. One group of 20 wildtype C57BL/6J mice (7 months old, both male and female) is also used as a normal control. After environmental adaptation in the lab for 5 days, the animals are treated with vehicle, control compound, or test compound, respectively, through oral gavage, once a day, six days a week, for 3 consecutive months. At the end of treatment, animals are subjected to behavioral evaluation, including the Y-maze test, the Morris water maze test, and other tests designed to measure short- and long-term memory. Finally, the animals are sacrificed and subjected to various biochemical and molecular evaluations, such as Aβ (including 1-40 and 1-42, soluble, plaque, and total), P-tau, GSK-3β, SYP, PSD95, NMDAR2B, p-NMDAR2B, CaMKII, p-CaMKII, and the like, and various parameters for inflammation and related physiological conditions.

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is a compound of Formula (I), or a pharmaceutically acceptable salt or ester thereof:

$$R^1R^2X\text{—}CR_2\text{—}CH_2\text{—}CH_2\text{—}SO_3H \quad (I)$$

where:
- $R^1$ and $R^2$ are independently a hydrogen of natural abundance or a protecting group, wherein said protecting group is isotope-enriched or non-isotope enriched, said protecting group being selected from acyl, carbonyl, thiocarbonyl, and carbamoyl groups, wherein at least one of $R^1$ and $R^2$ is a protecting group;
- X is a nitrogen of natural abundance or $^{15}N$, or a combination thereof; and
- R is a hydrogen of natural abundance, a deuterium (D) or a combination thereof;
- provided that at least one of X, R, $R^1$ and $R^2$ comprises an atom that is not of natural abundance;
- provided that the compound is not N-acetyl-3-amino-1-propanesulfonic acid.

2. The method of claim 1, wherein:
- R is a hydrogen of natural abundance and X is $^{15}N$;
- R is D and X is a nitrogen of natural abundance;
- R is D and X is $^{15}N$; or
- R is a hydrogen of natural abundance; X is a nitrogen of natural abundance; and at least one atom in $R^1$ and/or $R^2$ is not of natural abundance.

3. The method of claim 1, wherein:
- $R^1$ and $R^2$ are each a hydrogen of natural abundance; X is $^{15}N$; and
- R is a hydrogen of natural abundance, a deuterium (D) or a combination thereof.

4. The method of claim 1, wherein one of $R^1$ and $R^2$ is a hydrogen and one of $R^1$ and $R^2$ is a protecting group.

5. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is a compound of Formula (III), or a pharmaceutically acceptable salt or ester thereof:

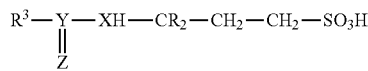

where:
- X is a nitrogen of natural abundance, a $^{15}N$ or a combination thereof;
- R is a hydrogen of natural abundance, a deuterium (D) or a combination thereof;
- Y is a carbon of natural abundance, a $^{13}C$ or a combination thereof;
- Z is a sulfur of natural abundance, an oxygen of natural abundance, an $^{18}O$, an $^{17}O$ or a combination thereof; and
- $R^3$ is a substituting group selected from substituted or unsubstituted alkyl, aryl, amino alkyl, amino arylalkyl, heterocyclyl, alkoxyl, alkylthio, alkylamino, acyloxyl, and thioacyloxyl;
- provided that at least one of X, R, Y and Z is not an atom of natural abundance;
- provided that the compound is not N-acetyl-3-amino-1-propanesulfonic acid.

6. The method of claim 5, wherein:
- R is not a hydrogen of natural abundance when X is a nitrogen of natural abundance;
- $R^3$, Y, and Z taken together form an acyl group connected to X, forming an amide bond linkage; or
- $R^3$ is a natural or unnatural amino acid residue and $R^3$, Y, and Z taken together form an acyl group connected to X, the acyl group being derived from a natural or unnatural amino acid.

7. The method of claim 6, wherein the natural or unnatural amino acid is an L-amino acid, a D-amino acid, or a mixture thereof.

8. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is a compound of Formula (IV), or a pharmaceutically acceptable salt or ester thereof:

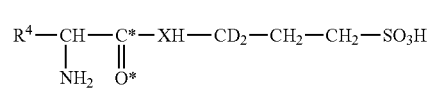

where:
- $R^4$ is a side chain of a natural or unnatural amino acid;
- O* is an oxygen atom of natural abundance, an $^{18}O$, an $^{17}O$ or a combination thereof; and
- C* is a carbon atom of natural abundance, a $^{13}C$ or a combination thereof;
- X is a nitrogen of natural abundance, a $^{15}N$ or a combination thereof;
- provided that at least one of O*, C*, and X is not an atom of natural abundance;
- provided that the compound is not N-acetyl-3-amino-1-propanesulfonic acid.

9. The method of claim 8, wherein the natural or unnatural amino acid is an L-amino acid, a D-amino acid, or a mixture thereof.

10. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is a compound of Formula (V), or a pharmaceutically acceptable salt or ester thereof:

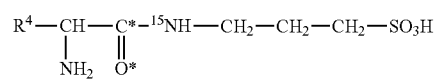

where:
- $R^4$ is a side chain of a natural or unnatural amino acid;
- O* is an oxygen atom of natural abundance, an $^{18}O$, an $^{17}O$ or a combination thereof; and
- C* is a carbon atom of natural abundance, a $^{13}C$ or a combination thereof;
- provided that the compound is not N-acetyl-3-amino-1-propanesulfonic acid.

11. The method of claim 10, wherein the natural or unnatural amino acid is an L-amino acid, a D-amino acid, or a mixture thereof.

12. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is a compound of Formula (VI), or a pharmaceutically acceptable salt or ester thereof:

$$R^4-CH-C^*-NH-CH_2-CH_2-CH_2-SO_3H \quad (VI)$$
$$\underset{NH_2}{|} \quad \underset{O^*}{\|}$$

where:
- $R^4$ is a side chain of a natural or unnatural amino acid;
- $O^\#$ is an oxygen atom of natural abundance, an $^{18}O$, an $^{17}O$ or a combination thereof;
- $C^\#$ is a carbon atom of natural abundance, a $^{13}C$ or a combination thereof;
- provided that at least one of $O^\#$ and $C^\#$ is an isotope-enriched atom;
- provided that the compound is not N-acetyl-3-amino-1-propanesulfonic acid.

13. The method of claim 12, wherein the natural or unnatural amino acid is an L-amino acid, a D-amino acid, or a mixture thereof.

14. The method of claim 1, wherein the compound is:

[Chemical structures of isotopically labeled amino acid-propanesulfonic acid conjugates, including variants with D$_2$, $^{13}C$, $^{17}O$, $^{18}O$, and $^{15}N$ labels of alanine, serine, valine, phenylalanine, histidine, and cysteine derivatives.]

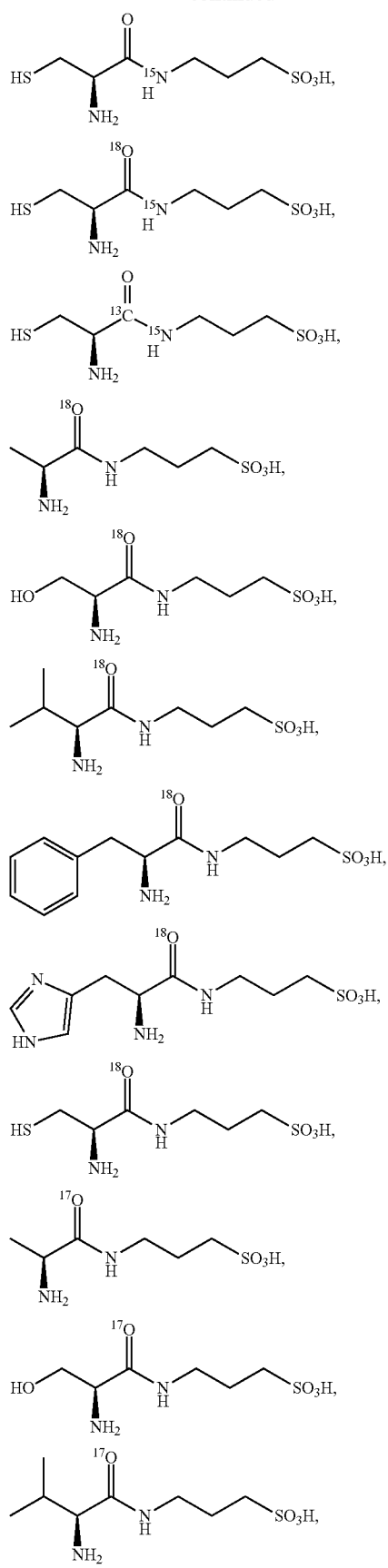
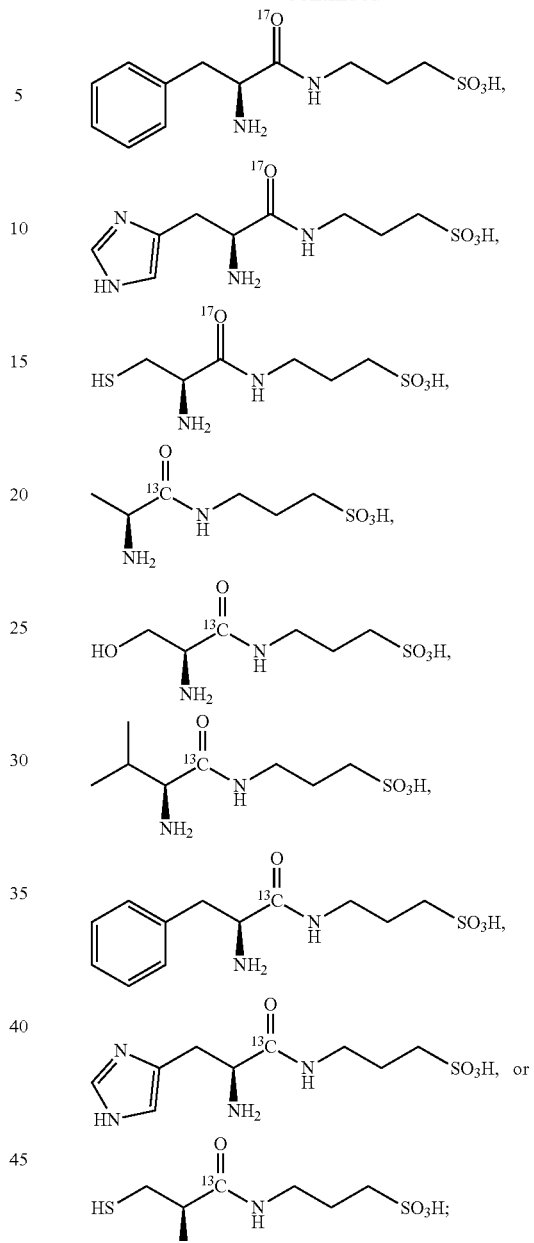

or a pharmaceutically acceptable salt or ester thereof.

15. The method of claim 1, wherein the level of isotope enrichment in the compound with isotopes that are not of natural abundance is about 2% or more, about 5% or more, about 10% or more, about 20% or more, about 50% or more, about 75% or more, about 90% or more, about 95% or more, or 100%.

16. The method of claim 1, wherein the subject is ApoE4 positive.

17. A method for treatment of cerebral amyloid angiopathy or hereditary cerebral hemorrhage in a subject in need thereof comprising administering to the subject a therapeutically effective amount of a compound, such that cerebral amyloid angiopathy or hereditary cerebral hemorrhage is treated in the subject, wherein the compound is

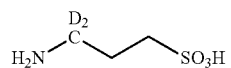
or a pharmaceutically acceptable salt or ester thereof.
* * * * *